United States Patent
Vaisberg et al.

(10) Patent No.: US 6,651,008 B1
(45) Date of Patent: *Nov. 18, 2003

(54) DATABASE SYSTEM INCLUDING COMPUTER CODE FOR PREDICTIVE CELLULAR BIOINFORMATICS

(75) Inventors: Eugeni A. Vaisberg, Foster City, CA (US); Cynthia L. Adams, Palo Alto, CA (US); James H. Sabry, San Francisco, CA (US); Anne M. Crompton, San Francisco, CA (US)

(73) Assignee: Cytokinetics, Inc., South San Francisco, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 09/721,154

(22) Filed: Nov. 21, 2000

Related U.S. Application Data

(63) Continuation of application No. 09/311,996, filed on May 14, 1999.

(51) Int. Cl.$^7$ .............................. G06F 19/00; C21Q 1/02
(52) U.S. Cl. ................................................ 702/21; 435/4
(58) Field of Search ................................ 702/21; 435/4

(56) References Cited

U.S. PATENT DOCUMENTS

| | | |
|---|---|---|
| 4,818,710 A | 4/1989 | Sutherland et al. |
| 4,922,092 A | 5/1990 | Rushbrooke et al. |
| 4,959,301 A | 9/1990 | Weaver et al. |
| 4,965,725 A | 10/1990 | Rutenberg |
| RE34,214 E | 4/1993 | Carlsson et al. |
| 5,287,272 A | 2/1994 | Rutenberg et al. |
| 5,326,691 A | 7/1994 | Hozier |
| 5,355,215 A | 10/1994 | Schroeder et al. |
| 5,526,258 A | 6/1996 | Bacus |
| 5,548,661 A | 8/1996 | Price et al. |
| 5,655,028 A | 8/1997 | Soll |
| 5,733,721 A | 3/1998 | Hemstreet, III et al. |
| 5,741,648 A | 4/1998 | Hemstreet et al. |
| 5,776,748 A | 7/1998 | Singhvi et al. |
| 5,777,888 A | 7/1998 | Rine et al. |
| 5,790,692 A | 8/1998 | Price et al. |
| 5,790,710 A | 8/1998 | Price et al. |
| 5,804,436 A | 9/1998 | Okun et al. |
| 5,856,665 A | 1/1999 | Price et al. |
| 5,893,095 A | 4/1999 | Jain et al. |
| 5,919,646 A | 7/1999 | Okun et al. |
| 5,932,872 A | 8/1999 | Price |
| 5,962,520 A | 10/1999 | Smith et al. |
| 5,976,825 A | 11/1999 | Hochman |
| 5,989,835 A | 11/1999 | Dunlay et al. |
| 5,991,028 A | 11/1999 | Cabib et al. |
| 5,995,143 A | 11/1999 | Price et al. |
| 6,007,996 A | 12/1999 | McNamara et al. |
| 6,008,010 A | 12/1999 | Greenberger et al. |
| 6,083,763 A | 7/2000 | Balch |
| 6,103,479 A | 8/2000 | Taylor |
| 6,146,830 A | 11/2000 | Friend et al. |
| 6,222,093 B1 | 4/2001 | Marton et al. |
| 6,345,115 B1 | 2/2002 | Ramm et al. |

FOREIGN PATENT DOCUMENTS

| | | |
|---|---|---|
| EP | 0468705 | 1/1992 |
| EP | 0317139 | 4/1998 |
| EP | 0902394 | 3/1999 |
| WO | WO 87/02802 | 5/1987 |
| WO | WO 93/21511 | 10/1993 |
| WO | WO 94/11841 | 5/1994 |
| WO | WO 95/10036 | 4/1995 |
| WO | WO 95/22749 | 8/1995 |
| WO | WO 96/01438 | 1/1996 |
| WO | WO 96/09605 | 3/1996 |
| WO | WO 97/20198 | 6/1997 |
| WO | WO 97/40055 | 10/1997 |
| WO | WO 97/43732 | 11/1997 |
| WO | WO 97/45730 | 12/1997 |
| WO | WO 98/05959 | 2/1998 |
| WO | WO 98/35256 | 8/1998 |
| WO | WO 98/38490 | 9/1998 |
| WO | WO 98/44333 | 10/1998 |
| WO | WO 98/45704 | 10/1998 |
| WO | WO 99/05323 | 2/1999 |
| WO | WO 99/08091 | 2/1999 |
| WO | WO 99/17116 | 4/1999 |
| WO | WO 99/39184 | 8/1999 |
| WO | WO 99/44062 | 9/1999 |
| WO | WO 99/54494 | 10/1999 |
| WO | WO 99/67739 | 12/1999 |
| WO | WO 00/03246 | 1/2000 |
| WO | WO 00/06774 | 2/2000 |
| WO | WO 00/17624 | 3/2000 |
| WO | WO 00/17643 | 3/2000 |
| WO | WO 00/17808 | 3/2000 |
| WO | WO 00/26408 | 5/2000 |
| WO | WO 00/29984 | 5/2000 |
| WO | WO 00/31534 | 6/2000 |
| WO | WO 00/43820 | 7/2000 |
| WO | WO 00/33250 | 8/2000 |
| WO | WO 00/49540 | 8/2000 |
| WO | WO 00/50872 | 8/2000 |
| WO | WO 00/60356 | 10/2000 |
| WO | WO 00/65472 | 11/2000 |
| WO | WO 00/70528 A2 | 11/2000 |

OTHER PUBLICATIONS

Giuliano et al. High–Content Screening: A New Approach to Easing Key Bottlenecks in the Drug Discovery Process. J. of Biom. Screening, 1997, vol. 2, No. 4, pp. 249–259.*

(List continued on next page.)

*Primary Examiner*—John S. Brusca
(74) *Attorney, Agent, or Firm*—Lauren L. Stevens, Esq.; Beyer Weaver & Thomas LLP

(57) ABSTRACT

According to the present invention, computer based techniques for using information technology in therapeutics or drug discovery. In an exemplary embodiment, computer based techniques for determining information about the properties of substances based upon information about structure of living or non-living cells exposed to substances are provided. Computer software according to the present invention enables researchers and/or scientists to identify promising candidates in the search for new and better medicines or treatments using, for example, a cellular informatics database.

5 Claims, 24 Drawing Sheets

OTHER PUBLICATIONS

Pauwel et al. The Application of Computerized Analysis of Nuclear Images and Multivariate Analysis to the Understanding of the Effects of Antineoplastic Agents and Their Mechanism of Action. Meth.Find.Exp.Clin.Pharmacol, 1993, vol. 15, No. 2, pp. 113–124.*

Blankenstein et al., "Modular concept of a laboratory on a chip for chemical and biochemical analysis," (1998) Biosensors & Bioelectronics 13:427–438.

Cseke, I., "A fast segmentation scheme for white blood cell images," (1992) IEEE, pp. 530–533.

Hartwell et al., "Integrating genetic approaches into the discovery of anticancer drugs," (1997) Science 278:1064–1068.

Hofland et al., "Role of tumor–derived fibroblasts in the growth of primary cultures of human breast–cancer cells: effects of epidermal growth factor and the somatostatin analogue octreotide," (1995) Int. J. Cancer: 60:93–99.

Ng et al., "Evaluating multi–dimensional indexing structures for images transformed by principal component analysis," Proceedings of SPIE, Bellingham, Spie, US (1996), vol. 2670, pp. 50–61.

Stearns et al., "Interleukin 10 (IL–10) inhibition of primary human prostate cells–induced angiogenesis: IL–10 stimulation of tissue inhibitor of metalloproteinase–1 and inhibition of matrix metalloproteinase (MMP)–2/MMP–9 secretion," (1999) Clin. Cancer Res. 5:189–196.

Takayama et al., "Patterning cells and their environments using multiple laminar fluid flows in capillary networks," (1999) Proc. Natl., Acad. Sci. USA 96:5545–5548.

Serbouti, S., et al., "Image Segmentation and Classification Methods to Detect Leukemias", (1991) Annual Int'l Conf. of IEEE Eng. In Medicine & Biology Soc., vol. 13, No. 1, pp. 0260–0261.

Adams, et al., "Cell Patterning on Glass and Polymeric Substrates", U.S. Provisional patent application No.: 60/138,119, Filed Jun. 7, 1999, 17 Pages.

Pauwels et al., "Determination of the Mechanism of Action of Anticancer Drugs by Means of the Computer– Assisted Microscope Image Analysis of Feulgen–Stained Nuclei", *J. Pharmacological and Toxicological Methods*. 37: 105–115 (1997).

Pauwels et al., "Monitoring Of Chemotherapy–Induced Morphonuclear Modifications By Means Of Digital Cell–Image Analysis", I. Cancer Res. Clin. Oncol., 119: 533–540 (1993).

Pauwels et al., "In Vitro Digital Cell Image Analysis of Morphonuclear Modifications Induced by Natural DNA–Interacting Anticancer Drugs in Three Neoplastic Cell Lines", *Meth. Find. Exp. Clin. Pharmacol.* . 17(3): 151–161 (1995).

Pauwels et al., "Combination of Computerized Morphonuclear and Multivariate Analyses to Characterize In Vitro the Antineoplastic Effect of Alkylating Agents", J. Pharmacol. and Toxicol. Methods, 33(1): 34–45 (1995).

Weinstein et al., " An Information–Intensive Approach to the Molecular Pharmacology of Cancer", *Science*, 275: 43–349 (Jan. 17, 1997).

Uria, et al., "Regulation of Collagenase–3 Expression in Human Breast Carcinomas is Mediated by Stromal–Epithelial Cell Interactions", Pub Med, Cancer Res 1997 Nov. 1; 57 (21):4882–8. Abstract.

Rubas, et al., "An Integrated Method to Determine Epithelial Transport and Bioactivity of Oral Drug Candidates in Vitro," *Pharmaceutical Research*, vol. 13, No. 1, pp. 23–27, 1996.

Sunblad et al., "The use of image analysis and automation for measuring mitotic index in apical confier meristems", © Oxford University Press 1998, Journal of Experimental Botany, vol. 49, No. 327, pp. 1749–1756.

Montironi R., et al., "Computer Cell Cycle and DNA Histogram Analyses in Image Cytometry in Breast Cancer", Journal of Clinical Pathology, GB, London, vol. 46, No. 9, Sep. 1993, pp. 795–800.

Giuliano K.A., et al., "Fluorescent–Protein Biosensors: New Tools for Drug Discovery", Trends in Biotechnology, GB, Elsevier Publications, Cambridge, vol. 16, No. 3, Mar. 1998, pp. 135–140.

Ravi Kapur, et al., "Design and Fabrication of Spatially Controlled Miniaturized Organ Systems From Stem Cells", U.S. Provisional patent application No.: 60/127,339, Filed Apr. 1, 1999, 21 Pages.

* cited by examiner

Step 204 of Fig. 2A

Step 214 of Fig. 2B

Step 216 of Fig. 2B

Conversion of morphometric parameters into nucleic acid code and clustering of the resulting sequences using Neighbor Joining method.

| Compound: | Count | Area | Perimeter | Length | Breadth | Fiber length | Fiber breadth | Shape factor | Ell. form factor | Inner radius | Outer radius | Mean radius | Equiv. radius | Equiv. sphere vol. | Equiv. prolate vol. | Equiv. oblate vol. | Equiv. sphere surface area | Average gray value | Total gray value | Optical density | Radial dispersion | Texture Difference Moment | EFA Harmonic 2, Semi-Major | EFA Harmonic 2, Semi-Minor |
|---|---|---|---|---|---|---|---|---|---|---|---|---|---|---|---|---|---|---|---|---|---|---|---|---|
| Control | t | t | t | t | t | t | t | t | t | t | t | t | t | t | t | t | t | t | t | t | t | a | t | t |
| Taxol | a | t | t | t | t | t | t | t | a | t | t | t | t | t | t | t | t | t | t | t | t | t | t | t |
| CD | c | a | a | t | a | t | t | c | a | a | a | a | a | a | a | a | t | a | a | a | t | a | a | g |
| Nocodozol | c | t | t | t | t | t | t | t | t | t | t | t | t | t | t | t | t | t | t | t | t | t | t | t |
| Staurosporine | g | g | c | a | a | t | a | a | t | g | a | a | a | t | g | g | g | a | a | t | a | t | a | a |
| Vinblastine | c | t | t | t | t | t | t | t | t | t | t | t | t | t | t | t | t | t | t | g | t | t | t | t |
| Hydroxyurea | g | t | t | t | t | t | t | g | t | t | t | t | t | t | t | t | t | t | t | c | t | a | t | t |

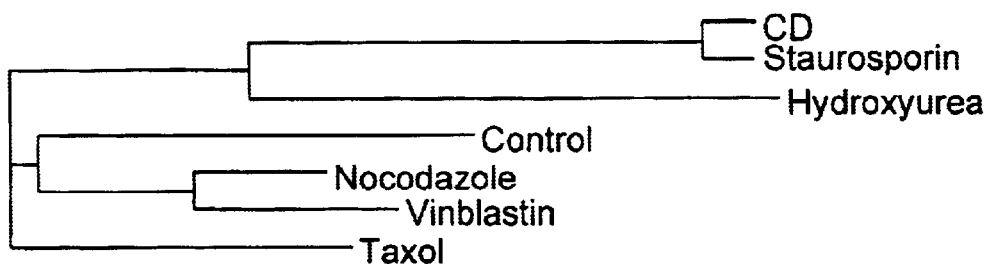

FIG. 13

Conversion of morphometric parameters into amino acid codes and clustering of the resulting sequences using Neighbor Joining method.

| | Count | Area | Perimeter | Length | Breadth | Fiber length | Fiber breadth | Shape factor | Ell. form factor | Inner radius | Outer radius | Mean radius | Equiv. radius | Equiv. sphere vol. | Equiv. prolate vol. | Equiv. oblate vol. | Equiv. sphere surface are | Average gray value | Total gray value | Optical density | Radial dispersion | Texture Difference Momei | EFA Harmonic 2, Semi-Major Axis | EFA Harmonic 2, Semi-Minor Ax | EFA Harmonic 2, Semi-Major A |
|---|---|---|---|---|---|---|---|---|---|---|---|---|---|---|---|---|---|---|---|---|---|---|---|---|---|
| Control | H | P | T | T | N | S | D | W | E | S | T | T | T | F | C | C | P | P | M | C | T | G | T | T | Y |
| Taxol | G | F | M | M | P | M | P | H | G | S | M | M | W | C | F | P | F | R | C | M | M | H | M | P | S |
| CD | F | G | G | G | M | G | M | K | A | G | G | G | G | G | G | G | G | H | G | G | G | M | G | V | H |
| Nocodozol | W | F | M | M | W | M | P | T | R | S | M | M | M | F | M | W | F | M | M | R | M | M | M | F | G |
| Staurosporine | N | V | A | G | G | M | G | G | Y | V | G | G | G | M | V | V | V | G | G | H | G | M | G | G | V |
| Vinblastine | F | W | W | M | W | W | C | W | D | S | M | W | W | M | M | M | W | M | V | E | M | M | M | F | P |
| Hydroxyurea | S | H | H | H | H | H | H | V | H | H | H | H | H | H | H | H | H | H | H | A | H | G | H | H | D |

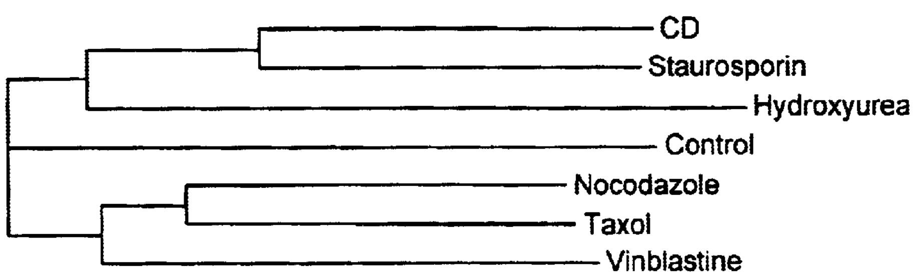

FIG. 14

SEQUENCE LISTING

```
<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Psuedo-sequence

<400> SEQUENCE: 1
tttttttttt tttttttttt tatt                                              24

<210> SEQ ID NO 2
<211> LENGTH: 24
<212> TYPE: DNA
<213> ORGANISM: Artificial Sequence
<220> FEATURE:
<223> OTHER INFORMATION: Psuedo-sequence

<400> SEQUENCE: 2
atttttttat tttttttttt tttt                                              24

<210> SEQ ID NO 3
<211> LENGTH: 24
<212> TYPE: DNA
<213> ORGANISM: Artificial Sequence
<220> FEATURE:
<223> OTHER INFORMATION: Psuedo-sequence

<400> SEQUENCE: 3
caaatattca aaaaaaataa atag                                              24

<210> SEQ ID NO 4
<211> LENGTH: 24
<212> TYPE: DNA
<213> ORGANISM: Artificial Sequence
<220> FEATURE:
<223> OTHER INFORMATION: Psuedo-sequence

<400> SEQUENCE: 4
cttttttttt tttttttttt tttt                                              24

<210> SEQ ID NO 5
<211> LENGTH: 24
<212> TYPE: DNA
<213> ORGANISM: Artificial Sequence
<220> FEATURE:
<223> OTHER INFORMATION: Psuedo-sequence

<400> SEQUENCE: 5
ggcaataatg aaatgggaat ataa                                              24

<210> SEQ ID NO 6
<211> LENGTH: 24
<212> TYPE: DNA
<213> ORGANISM: Artificial Sequence
<220> FEATURE:
<223> OTHER INFORMATION: Psuedo-sequence
```

-continued

```
<400> SEQUENCE: 6 ctttttttttt ttttttttgt tttt                                            24

<210> SEQ ID NO 7
<211> LENGTH: 24
<212> TYPE: DNA
<213> ORGANISM: Artificial Sequence
<220> FEATURE:
<223> OTHER INFORMATION: Psuedo-sequence

<400> SEQUENCE: 7 gtttttttgtt ttttttttc tatt                                             24

<210> SEQ ID NO 8
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 8

His Pro Thr Thr Asn Ser Asp Trp Glu Ser Thr Thr Thr Phe Cys Cys
 1               5                  10                  15

Pro Pro Met Cys Thr Gly Thr Thr Tyr
            20                  25

<210> SEQ ID NO 9
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 9

Gly Phe Met Met Pro Met Pro His Gly Ser Met Met Trp Cys Phe Pro
 1               5                  10                  15

Phe Arg Cys Met Met His Met Pro Ser
            20                  25

<210> SEQ ID NO 10
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 10

Phe Gly Gly Gly Met Gly Met Lys Ala Gly Gly Gly Gly Gly Gly Gly
 1               5                  10                  15

Gly His Gly Gly Gly Met Gly Val His
            20                  25

<210> SEQ ID NO 11
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 11

Trp Phe Met Met Trp Met Pro Thr Arg Ser Met Met Met Phe Met Trp
 1               5                  10                  15

Phe Met Met Arg Met Met Met Phe Gly
            20                  25
```

-continued

```
<210> SEQ ID NO 12
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 12

Asn Val Ala Gly Gly Met Gly Gly Tyr Val Gly Gly Gly Met Val Val
 1               5                  10                  15

Val Gly Gly His Gly Met Gly Gly Val
            20                  25

<210> SEQ ID NO 13
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 13

Phe Trp Trp Met Trp Trp Cys Trp Asp Ser Met Trp Trp Met Met Met
 1               5                  10                  15

Trp Met Val Glu Met Met Met Phe Pro
            20                  25

<210> SEQ ID NO 14
<211> LENGTH: 25
<212> TYPE: PRT
<213> ORGANISM: Artificial Sequence
<220> FEATURE:
<223> OTHER INFORMATION: Psuedo-sequence

<400> SEQUENCE: 14

Ser His His His His His Val His His His His His His His
 1               5                  10                  15

His His His Ala His Gly His His Asp
            20                  25
```

DATABASE SYSTEM INCLUDING COMPUTER CODE FOR PREDICTIVE CELLULAR BIOINFORMATICS

CROSS-REFERENCES TO RELATED APPLICATIONS

"This is a Continuation application of prior application Ser. No. 09/311,996 filed on May 14, 1999, designated the United States, the disclosure of which is incorporated herein by reference."

1. U.S. patent application Ser. No. 09/310,879, James H. Sabry, et. al., titled, "A DATABASE METHOD FOR PREDICTIVE CELLULAR BIOINFORMATICS,";

2. U.S. patent application Ser. No. 09/311,890, James H. Sabry, et. al., titled, "A DATABASE SYSTEM FOR PREDICTIVE CELLULAR BIOINFORMATICS,";

3. U.S. patent application Ser. No. 60/134,104, Cynthia L. Adams, etc. al., titled, "A DATABASE SYSTEM AND USER INTERFACE FOR PREDICTIVE CELLULAR BIOINFORMATICS,"; and 4. U.S. patent application Ser. No. 09/311,996, Eugeni A. Vaisberg, et. al., titled, "A DATABASE SYSTEM INCLUDING COMPUTER CODE FOR PREDICTIVE CELLULAR BIOINFORMATICS".

COPYRIGHT NOTICE

A portion of the disclosure of this patent document contains material which is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

BACKGROUND OF THE INVENTION

The present invention provides information technology based techniques including computer software in therapeutics or drug discovery. In an exemplary embodiment, the present invention provides software for determining information about properties of substances based upon information about structures of living, fixed or non-living cells, or cell fractions. Computer code according to the present invention enable researchers and scientists to identify promising candidates in the search for new and better medicines and medical techniques.

For a long time, researchers in the pharmaceutical field have sought for better ways of searching for substances possessing properties which make them suitable as medicines. In the early days, researches generally relied upon dyes, or extracts from plants, or microbiological broths for such substances. Examples of such substances include aspirin, and antibiotics.

Substances having desirable bio-active properties, however, are often difficult to isolate and identify. Advances in organic chemistry such as rapid chemical synthesis techniques have increased the number of compounds that researchers want to test for biological activity. Conventionally, substances were often tested on humans or animal subjects to determine biological activity. While results from such tests can be highly predictive, these types of tests can be time consuming, limiting the progress of the testing.

There have been some attempts to use image acquisition techniques to screen for large numbers of molecules based upon cell information. Conventional image acquisition systems exist that generally capture digitized images of discrete cells for identification purposes. Identification often occurs during the image capturing step, which is limiting. In most cases, these conventional techniques cannot comprehensively provide for complete cellular information but can only be used to identify a fairly limited set of information.

What is needed are techniques for collecting and managing information useful in finding the effects of manipulations on cell function, response or behavior.

SUMMARY OF THE INVENTION

According to the present invention, techniques for using information technology in therapeutics or drug discovery. In an exemplary embodiment, computer software for determining information about the properties of substances based upon information about a structure or the morphology of living, fixed or dead cells (e.g., elements, cell portions and cell fractions) exposed to substances are provided. Computer software according to the present invention enables researchers and/or scientists to identify promising candidates in the search for new and better medicines or treatments using, for example, a cellular informatics database.

According to the present invention, a computer program for identification and verification of biological properties of substances can include code that administers a sample of the substance to a cell. The code determines one or more features for two or more cell components, or markers, in the presence of the substance. The code can form one or more descriptors from the features. Descriptors can be formed by combining features of two or more cell components as identified using the markers. The code can then search one or more descriptors obtained from prior administered substances upon cells in order to locate descriptors having a relationship to the descriptors noted for the substance under study. The code predicts properties of the administered substance based upon the properties of the prior administered substances using the relationship between the descriptors. The code can provide for identifying properties of substances based upon effects on cell characteristics. Candidate drug mechanisms of action, potency, specificity, pharmacodynamic, and pharmacokinetic parameters, toxicity, and the like can be used as substance properties.

In another embodiment according to the present invention, computer programs for animal model selection, clinical trial design and patient management can be provided.

In a further embodiment according to the present invention, techniques for using cellular information in predictive methods for acquiring, analyzing and interpreting cellular data are incorporated into a computer program product including code. In one such embodiment, code for predicting properties of an unknown substance based upon information about effects of one or more known substances on a cell population is provided. The code performs a variety of tasks, such as populating a database with descriptors of cells subjected to known substances. Such descriptors can be determined from imaging the cell population. However, in some embodiments, descriptors can be derived by measurements and combinations of measurements and the like. The code determines descriptors for the unknown substance from imaging a second cell population. The second cell population has been treated with the unknown substance. Then, the code can determine a relationship between the descriptors determined from the unknown substance with the descriptors determined from the known substance. From this relationship, an inference can be made about the unknown substance.

In a yet further embodiment according to the present invention, a computer program for determining properties of a manipulation based upon effects of the manipulation on one or more cell fractions. The computer program includes code that can provide the manipulation to the cell fractions. The code can also determine one or more features of markers corresponding to cell components within the cell fractions in the presence of the manipulation. Code for forming descriptors from the features is also included. Code for searching in a database in order to locate descriptors based upon at least one of the descriptors obtained from the manipulation is also included. The computer program can include code for determining, based upon the descriptors located in the database, properties of the manipulation.

Moreover, the present invention provides computer software for mapping a manipulation of cells based upon a morphological characteristic. The computer software includes code for providing a plurality of cells, e.g., dead, live, cell fragments, cell components, cell substructures. The software also includes code for manipulating the plurality of cells, where manipulation occurs using a source(s) from one or a combination selected from an electrical source, a chemical source, a thermal source, a gravitational source, a nuclear source, a temporal source, and a biological source. The software code captures a morphological value from the plurality of cells. The morphological value can include one or any combination of characteristics such as a cell count, an area, a perimeter, a length, a breadth, a fiber length, a fiber breadth, a shape factor, an elliptical form factor, an inner radius, an outer radius, a mean radius, an equivalent radius, an equivalent sphere volume, an equivalent prolate volume, an equivalent oblate volume, an equivalent sphere surface area, an average gray value, a total gray value, and an optical density. The software code also assigns a degree of presence of the morphological value, and stores the morphological value from the plurality of cells. These values can be used for a statistical analysis to produce a statistical profile.

Still further, the present invention provides a computer program product for populating a database with manipulated biological information, e.g., cellular enzymatic activities, cellular cascades, cellular promoters, transcription factors, translation factors, cell cycle stage and apoptosis. The computer program product includes code for providing a plurality of cells in various stages of the cell cycle, where the stages of the cell cycle may include at least one selected from interphase, G0 phase, G1 phase, S phase, G2 phase, M phase which itself includes prophase, prometaphase, metaphase, anaphase, and telophase. The computer program also includes code for manipulating each of the cells in the various stages of the cell cycle. The computer program includes code for capturing (e.g., image acquisition) an image of the plurality of manipulated cells where the code for capturing provides a morphometric characteristic of the manipulated cells. The computer program product also includes code for populating a database with the morphometric characteristic of the plurality of manipulated cells. Accordingly, the present invention provides software for populating a database, which can be queried.

Numerous benefits are achieved by way of the present invention over conventional techniques. The present invention can provide techniques for predictive cellular bioinformatics that can stream line a number of important decisions made in the drug discovery industry, medical diagnostics and biological research. The present invention can be implemented on conventional hardware including databases. In other aspects, the present invention can find useful information about substances as well as cells or portions of cells, especially morphology. Embodiments can provide a holistic approach to cell based drug discovery that enables the understanding of properties of substances based on their overall effects on cell biology. The properties include, among others, clinical uses and descriptors, human and veterinary diagnostic uses and tests, or human and veterinary prognostic uses and tests. Depending upon the embodiment, one or more of these advantages may be present. These and other benefits are described throughout the present specification.

A further understanding of the nature and advantages of the invention herein may be realized by reference to the remaining portions of the specification and the attached drawings.

BRIEF DESCRIPTION OF THE DRAWINGS

FIGS. 2A–2K illustrate representative block diagrams of simplified process steps in a particular embodiment according to the present invention;

FIG. 13 illustrates examples of the generation of pseudosequences, showing SEQ ID NOs: 1–7 sequentially, and clustering in a particular embodiment according to the present invention.

FIG. 14 illustrates examples of the generation of pseudosequences, showing SEQ ID NOs: 8–14 sequentially, and clustering in a particular embodiment according to the present invention.

DESCRIPTION OF THE SPECIFIC EMBODIMENTS

According to the present invention, techniques for using information technology in therapeutics or drug discovery. In an exemplary embodiment, techniques for determining information about the properties of substances based upon information about the structure of living, fixed or non-living cells exposed to the substances are provided. Computer software according to the present invention enables researchers and/or scientists to identify promising candidates in the search for new and better medicines or treatments using, for example, a cellular informatics database. An embodiment according to the present invention is marketed under the name Cytometrix™, which is not intended to be limiting.

In a particular embodiment according to the present invention, a cellular informatics database is provided. Embodiments according to the present invention can provide techniques for predicting candidate drug mechanisms of action, potency, specificity, structure, toxicity and the like. In some embodiments, substances or other manipulations can be used for target identification and validation. Embodiments can be useful in areas such as animal model selection, clinical trial design and patient management, including prognostics, drug response prediction and adverse effect prediction.

Figure 1:
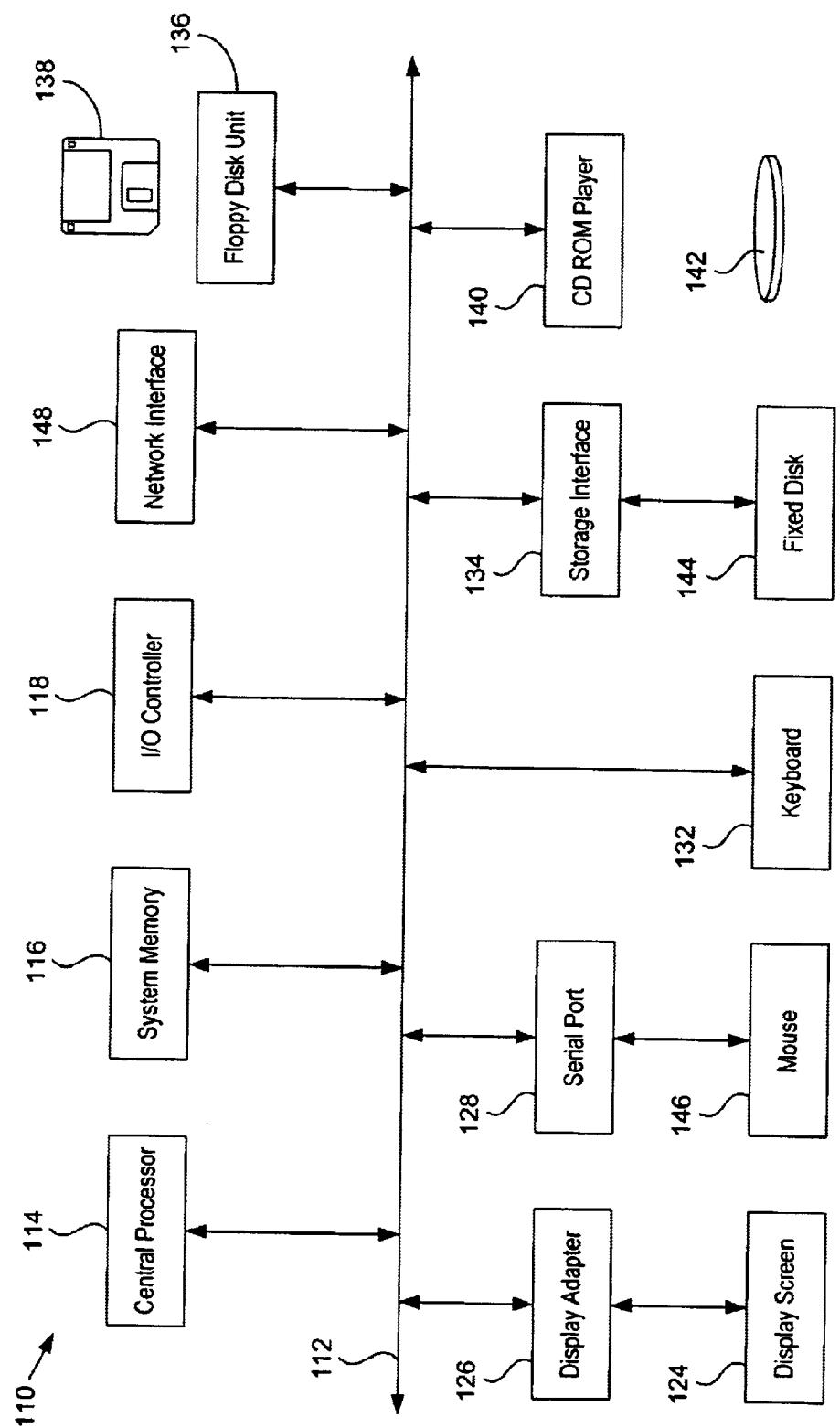
FIG. 1 illustrates a block diagram of a system according to an embodiment according to the present invention.

FIG. 1 depicts a block diagram of a host computer system 110 suitable for implementing the present invention. This diagram is merely an illustration and should not limit the scope of the claims herein. One of ordinary skill in the art would recognize other variations, modifications, and alternatives. Host computer system 110 includes a bus 112 which interconnects major subsystems such as a central processor 114, a system memory 116 (typically RAM), an input/output (I/O) controller 118, an external device such as a display screen 124 via a display adapter 126, a keyboard 132 and a mouse 146 via an I/O controller 118, a SCSI host adapter (not shown), and a floppy disk drive 136 operative to receive a floppy disk 138. Storage Interface 134 may act as a storage interface to a fixed disk drive 144 or a CD-ROM player 140 operative to receive a CD-ROM 142. Fixed disk 144 may be a part of host computer system 110 or may be separate and accessed through other interface systems.

The system has other features. A network interface 148 may provide a direct connection to a remote server via a telephone link or to the Internet. Network interface 148 may also connect to a local area network (LAN) or other network interconnecting many computer systems. Many other devices or subsystems (not shown) may be connected in a similar manner. Also, it is not necessary for all of the devices shown in FIG. 1 to be present to practice the present invention, as discussed below. The devices and subsystems may be interconnected in different ways from that shown in FIG. 1. The operation of a computer system such as that shown in FIG. 1 is readily known in the art and is not discussed in detail in this application. Code to implement the present invention, may be operably disposed or stored in computer-readable storage media such as system memory 116, fixed disk 144, CD-ROM 140, or floppy disk 138.

Although the above has been described generally in terms of specific hardware, it would be readily apparent to one of ordinary skill in the art that many system types, configurations, and combinations of the above devices are suitable for use in light of the present disclosure. Of course, the types of system elements used depend highly upon the application. Other examples of system can be found in co-pending application U.S. application Ser. No. 09/311,890, which has been noted above.

Figure 2A:
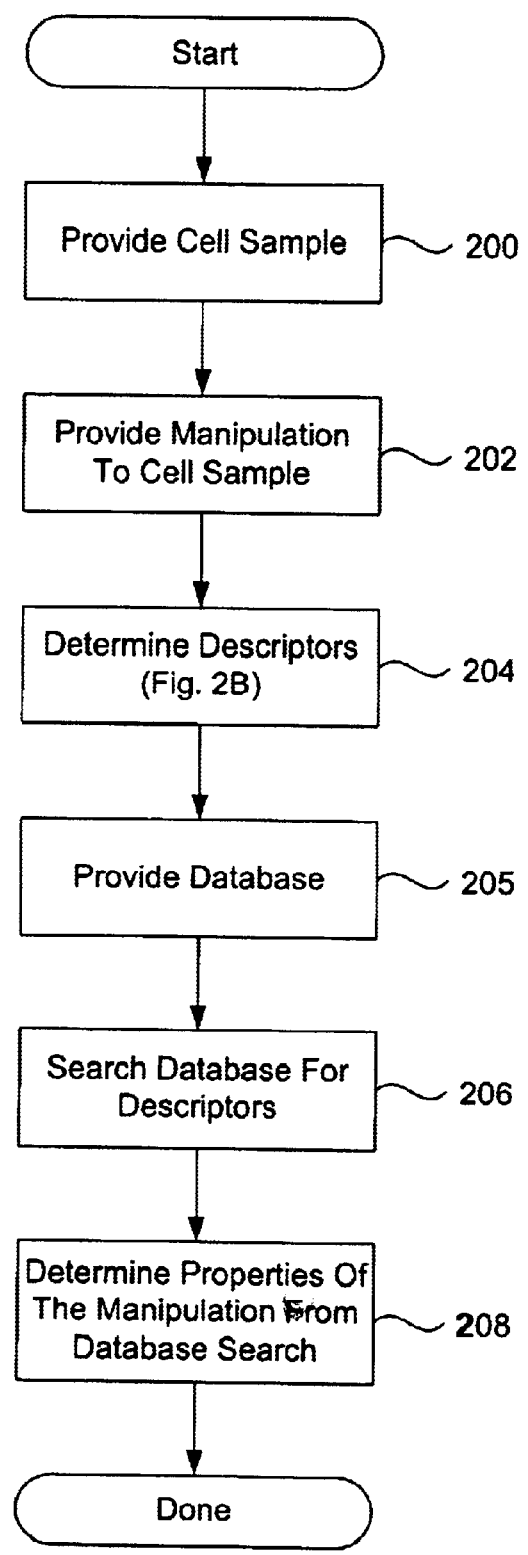

FIG. 2A illustrates a representative block flow diagram of simplified process steps of a method for determining properties of a manipulation based upon effects of the manipulation on one or more portions of one or more cells in a particular embodiment according to the present invention. This diagram is merely an illustration and should not limit the scope of the claims herein. One of ordinary skill in the art would recognize other variations, modifications, and alternatives. In a step 200, one or more samples of cells can be provided. These cells can be live, dead, or cell fractions. The cells also can be in one of many cell cycle stages, including G0, G1, S, G2 or M phase, which itself includes the following mitotic stages: prophase, prometaphase, metaphase, anaphase, and telophase. Cell components may be tracked using one or more markers. In a presently preferable embodiment, many useful and novel cell markers can be used.

Cell components tracked in presently preferable embodiments can include proteins, protein modifications, genetically manipulated proteins, exogenous proteins, enzymatic activities, nucleic acids, lipids, carbohydrates, organic and inorganic ion concentrations, sub-cellular structures, organelles, plasma membrane, adhesion complex, ion channels, ion pumps, integral membrane proteins, cell surface receptors, G-protein coupled receptors, tyrosine kinase receptors, nuclear membrane receptors, ECM binding complexes, endocytotic machinery, exocytotic machinery, lysosomes, peroxisomes, vacuoles, mitochondria, golgi apparatus, cytoskeletal filament network, endoplasmic reticulum, nuclear membrane, proteosome apparatus, chromatin, nucleolus, cytoplasm, cytoplasmic signaling apparatus, microbe specializations and plant specializations.

The following table illustrates some markers and cell components commonly used by embodiments according to the present invention. Other markers can be used in various embodiments without departing from the scope of the invention.

| Cell component | Marker | Disease State |
| --- | --- | --- |
| Plasma membrane (including overall cell shape) | Carbocyanine dyes Phosphatidylserine Various lipids Glycoproteins | Apoptosis-Cancer Apoptosis-Neural degenerative Ds |
| Adhesion complexes | Cadherins Integrins Occludin Gap junction ERM proteins CAMs Catenins Desmosomes | Thrombosis Metastasis Wound healing Inflammatory Ds Dermatologic Ds |
| Ion Channels and Pumps | Na/K Atpase Calcium channels Serotonin reuptake pump CFTR | Cystic fibrosis Depression Congestive Heart Failure Epilepsy |
| G coupled receptors | β adrenergic receptor Angiotensin receptor | Hypertension Heart Failure Angina |
| Tyrosine kinase receptors | PDGF receptor FGF receptor IGF receptor | Cancer Would healing Angiogenesis Cerebrovascular Ds |
| ECM binding complexes | Dystroglycan Syndecan | Muscular Dystrophy |
| Endocytotic machinery | Clathrin Adaptor proteins COPs Presenilins Dynamin | Alzheimer's Ds |
| Exocytotic machinery | SNAREs Vesicles | Epilepsy Tetanus Systemic Inflammation Allergic Reactions |
| Lysosomes | Acid phosphatase Transferrin | Viral diseases |

-continued

| Cell component | Marker | Disease State |
|---|---|---|
| Peroxisomes/ Vacuoles | | Neural degenerative Ds |
| Mitochondria | Caspases | Apoptosis |
| | Apoptosis inducing factor | Neural degenerative Ds Mitochondrial |
| | F1 ATPase | Cytopathies |
| | Fluorescein Cyclo-oxygenase | Inflammatory Ds |
| Golgi Apparatus | Lens Culinaris DiOC6 carbocyanine dye COPs | |
| Cytoskeletal Filament Networks | Microtubules | Cancer |
| | Actin | Neural degenerative Ds |
| | Intermediate Filaments | Inflammatory Ds |
| | Kinesin, dynein, myosin | Cardiovascular Ds |
| | Microtubule associated proteins | Skin Ds |
| | Actin binding proteins Rac/Rho Keratins | |
| Endoplasmic Reticulum | SNARE | Neural degenerative Ds |
| | PDI Ribosomes | |
| Nuclear Membrane | Lamins Nuclear Pore Complex | Cancer |
| Proteosome Apparatus | Ubiquityl transferases | Cancer |
| Chromatin | DNA | Cancer |
| | Histone proteins | Aging |
| | Histone deacetylases Telomerases | |
| Nucleolus | Phase markers | |
| Cytoplasm | Intermediary Metabolic Enzymes BRCA1 | Cancer |
| Cytoplasmic Signaling Apparatus | Calcium | Cardiovascular Ds |
| | Camp | Migraine |
| | PKC | Apoptosis |
| | pH | Cancer |
| Microbe Specializations | Flagella Cilia Cell Wall components: Chitin synthase | Infectious Ds |
| Plant specializations | Choloroplast Cell Wall components | Crop Protection |

Then, in a step 202, one or more samples of the manipulation can be provided to one or more of the cells or cell fractions. Manipulations can comprise chemical, biological, mechanical, thermal, electromagnetic, gravitational, nuclear, temporal factors, and the like. For example, manipulations could include exposure to chemical compounds, including compounds of known biological activity such as therapeutics or drugs, or also compounds of unknown biological activity. Or exposure to biologics that may or may not be used as drugs such as hormones, growth factors, antibodies, or extracellular matrix components. Or exposure to biologics such as infective materials such as viruses that may be naturally occurring viruses or viruses engineered to express exogenous genes at various levels. Bioengineered viruses are one example of manipulations via gene transfer. Other means of gene transfer are well known in the art and include but are not limited to electroporation, calcium phosphate precipitation, and lipid-based transfection. Manipulations could also include delivery of antisense polynucleotides by similar means as gene transfection. Other genetic manipulations include gene knock-outs gene over-expression or gene mutations. Manipulations also could include cell fusion. Physical manipulations could include exposing cells to shear stress under different rates of fluid flow, exposure of cells to different temperatures, exposure of cells to vacuum or positive pressure, or exposure of cells to sonication. Manipulations could also include applying centrifugal force. Manipulations could also include changes in gravitational force, including sub-gravitation. Manipulations could include application of a constant or pulsed electrical current. Manipulations could also include irradiation. Manipulations could also include photobleaching which in some embodiments may include prior addition of a substance that would specifically mark areas to be photobleached by subsequent light exposure. In addition, these types of manipulations may be varied as to time of exposure, or cells could be subjected to multiple manipulations in various combinations and orders of addition. Of course, the type of manipulation used depends upon the application.

Then, in a step 204, one or more descriptors of a state in the portions of the cells in the presence of the manipulation can be determined based upon the images collected by the imaging system. Descriptors can comprise scalar or vector values, representing quantities such as area, perimeter, dimensions, intensity, aspect ratios, and the like. Other types of descriptors include one or any combination of characteristics such as a cell count, an area, a perimeter, a length, a breadth, a fiber length, a fiber breadth, a shape factor, an elliptical form factor, an inner radius, an outer radius, a mean radius, an equivalent radius, an equivalent sphere volume, an equivalent prolate volume, an equivalent oblate volume, an equivalent sphere surface area, an average intensity, a total intensity and an optical density. In some embodiments, descriptors can include averages or standard deviation values, or frequency statistics from other descriptors collected across a population of cells. In some embodiments, descriptors can be reduced using techniques such as principal component analysis and the like. A presently preferable embodiment uses descriptors selected from the following table. Other descriptors can also be used without departing from the scope of the invention.

| Name of Parameter | Explanation/Comments |
|---|---|
| Count | Number of objects |
| Area | |
| Perimeter | |
| Length | X axis |
| Width | Y axis |
| Shape Factor | Measure of roundness of an object |
| Height | Z axis |
| Radius | |
| Distribution of Brightness | |
| Radius of Dispersion | Measure of how dispersed the marker is from its centroid |
| Centroid location | x-y position of center of mass |
| Number of holes in closed objects | Derivatives of this measurement might include, for example, Euler number (= number of objects − number of holes) |
| Elliptical Fourier Analysis (EFA) | Multiple frequencies that describe the shape of a closed object |
| Wavelet Analysis | As in EFA, but using wavelet transform |
| Interobject Orientation | Polar Coordinate analysis of relative location |
| Distribution Interobject Distances | Including statistical characteristics |
| Spectral Output | Measures the wavelength spectrum of the reporter dye. Includes FRET |
| Optical density | Absorbance of light |
| Phase density | Phase shifting of light |
| Reflection interference | Measure of the distance of the cell membrane from the surface of the substrate |

-continued

| Name of Parameter | Explanation/Comments |
| --- | --- |
| 1, 2 and 3 dimensional Fourier Analysis | Spatial frequency analysis of non closed objects |
| 1, 2 and 3 dimensional Wavelet Analysis | Spatial frequency analysis of non closed objects |
| Eccentricity | The eccentricity of the ellipse that has the same second moments as the region. A measure of object elongation. |
| Long axis/Short Axis Length | Another measure of object elongation. |
| Convex perimeter | Perimeter of the smallest convex polygon surrounding an object |
| Convex area | Area of the smallest convex polygon surrounding an object |
| Solidity | Ratio of polygon bounding box area to object area. |
| Extent | proportion of pixels in the bounding box that are also in the region |
| Granularity | |
| Pattern matching | Significance of similarity to reference pattern |
| Volume measurements | As above, but adding a z axis |

Then, in a step 205, a database of cell information can be provided. Next, in a step 206, a plurality of descriptors can be searched from a database of cell information in order to locate descriptors based upon one of the descriptors of the manipulation. Then, in a step 208, properties of the manipulation are determined based upon the properties of the located descriptors. Properties can comprise toxicity, specificity against a subset of tumors, mechanisms of chemical activity, mechanisms of biological activity, structure, adverse biological effects, biological pathways, clinical effects, cellular availability, pharmacological availability, pharmacodynamic properties, clinical uses and descriptors, pharmacological properties, such as absorption, excretion, distribution, metabolism and the like.

In a particular embodiment, step 206 comprises determining matching descriptors in the database corresponding to a prior administration of the manipulation to the descriptors of the present administration of the manipulation. In a particular embodiment according to the present invention, measurements of scalar values can provide predictive information. A database can be provided having one or more "cellular fingerprints" comprised of descriptors of cell-substance interactions of drugs having known mechanisms of action with cells. Such fingerprints can be analyzed, classified and/or compared using a plurality of techniques, such as statistical classification and clustering, heuristic classification techniques, a technique of creating "phylogenetic trees" based on various distance measures between cellular fingerprints from various drugs. In a present embodiment, scalar, numeric values can be converted into a nucleotide or amino acid letter. Once converted into a corresponding nucleotide representation, the fingerprints can be analyzed and compared using software and algorithms known in the art for genetic and peptide sequence comparisons, such as GCG, a product of Genetics Computer Group, with company headquarters in Madison Wis. In an alternative embodiment, numeric values for the fingerprints can be used by comparison techniques. A phylogenetic tree can be created that illustrates a statistical significance of the similarity between fingerprints for the drugs in the database. Because the drugs used to build the initial database are of known mechanism, it can be determined whether a particular scalar value in a fingerprint is statistically predictive. Finally, a compound fingerprint with no known mechanism of action can be queried against the database and be statistically compared and classified among the drugs in the database that the compound most resembles.

In a particular embodiment, relationships between measured morphological properties of images and physiological conditions can be determined. Relationships can include, for example, treatment of different cell lines with chemical compounds, or comparing cells from a patient with control cells, and the like. In a presently preferable embodiment, a clustering can be performed on acquired image feature vectors. Some embodiments can comprise statistical and neural network—based approaches to perform clustering and fingerprinting of various features. The foregoing is provided as merely an example, and is not intended to limit the scope of the present invention. Other techniques can be included for different types of data.

In some embodiments, clustering and fingerprinting can be performed on features extracted from cell images. In a presently preferable embodiment, procedures for comparisons and phylogenetic analysis of biological sequences can be applied to data obtained from imaging cells.

Select embodiments comprising such approaches enable the use of a broad array of sophisticated algorithms to compare, analyze, and cluster gene and protein sequences. Many programs performing this task are known to those of ordinary skill in the art.

Embodiments can perform such analysis based upon factors such as numerical value, statistical properties, relationships with other values, and the like. In a particular embodiment, numbers in a numerical features vector can be substituted by one or more of nucleic acid or amino acid codes. Resulting "pseudo-sequences" can be subjected to analysis by a sequence comparison and clustering program. Depending upon the application, many different ways of using the database can be provided. Further details of a step of manipulation are noted more particular below.

Figure 2B:
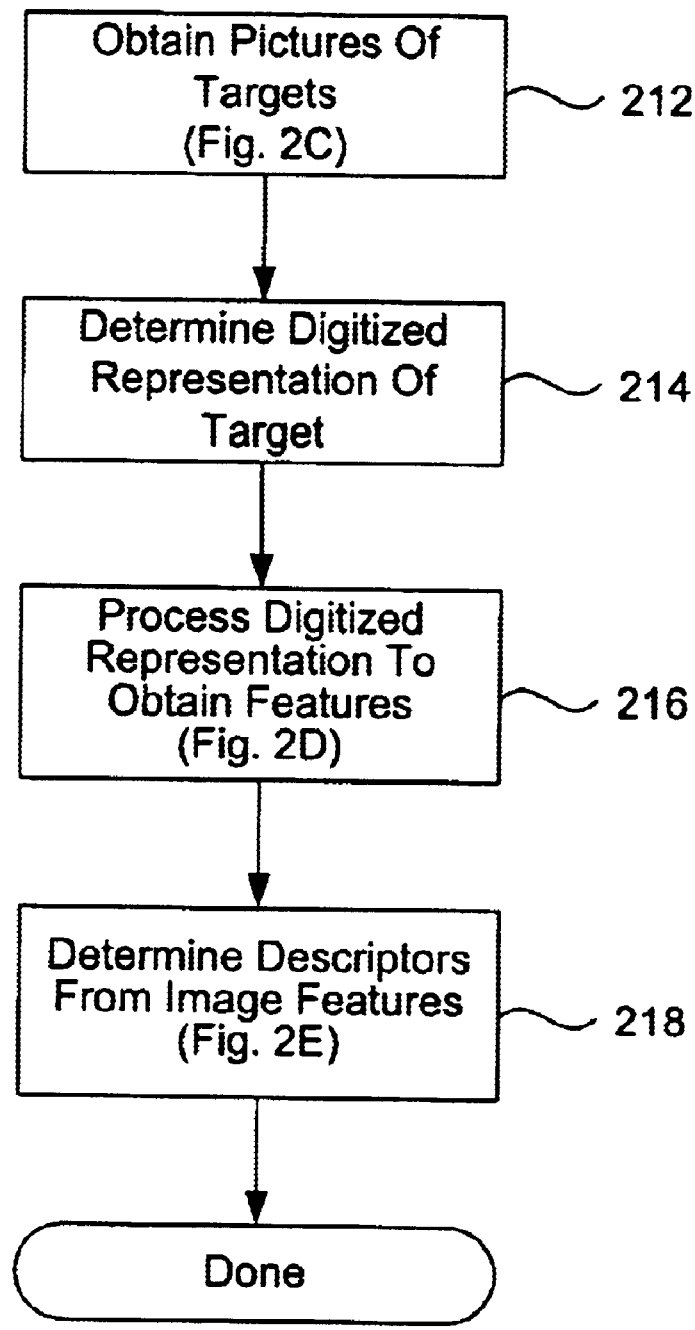

FIG. 2B illustrates a representative block flow diagram of simplified process steps for determining one or more descriptors of a state in the portions of the cells in the presence of the manipulation of step 204 of FIG. 2A in a particular embodiment according to the present invention. This diagram is merely an illustration and should not limit the scope of the claims herein. One of ordinary skill in the art would recognize other variations, modifications, and alternatives. In a step 212, a picture of a target is obtained. A target can be one or more cells, or portions of cells in select embodiments according to the invention. Then, in a step 214, a digitized representation of the picture obtained in step 212 is determined. In some embodiments, steps 214 and step 212 can comprise a single step. These embodiments use a digital imaging means such as a digital camera, to obtain a digital image of the target directly. Next, in a step 216, the digital representation of the image is processed to obtain image features. Image features can include such quantities as area, perimeter, dimensions, intensity, gray level, aspect ratios, and the like. Then, in a step 218 descriptors can be determined from the image features. Descriptors can comprise scalar or vector quantities and can comprise the image descriptors themselves, as well as derived quantities, such as shape factor derived by a relationship $4\pi*\text{area/perimeter}$, and the like.

In a preferred embodiment, cells can be placed onto a microscope, such as a Zeiss microscope, or its equivalent as known in the art. A starting point, named Site A1, is identified to the microscope. A plurality of exposure parameters can be optimized for automated image collection and analysis. The microscope can automatically move to a new well, automatically focus, collect one or more images, move to a next well, and repeat this process for designated wells in a multiple well plate. A file having a size and an intensity distribution measurement for each color and rank for each well can then be created for the images acquired. Based on this information, a user or a computer can revisit sites of interest to collect more data, if desired, or to verify automated analysis. In a presently preferred embodiment, image automatic focus and acquisition can be done using computer software controlling the internal Z-motor of the microscope. Images are taken using a 10×, 20×, or 40× air long working distance objectives. Sometimes multiple images are collected per well. Image exposure times can be optimized for each fluorescent marker and cell line. The same exposure time can be used for each cell line and fluorescent marker to acquire data.

Figure 2C:
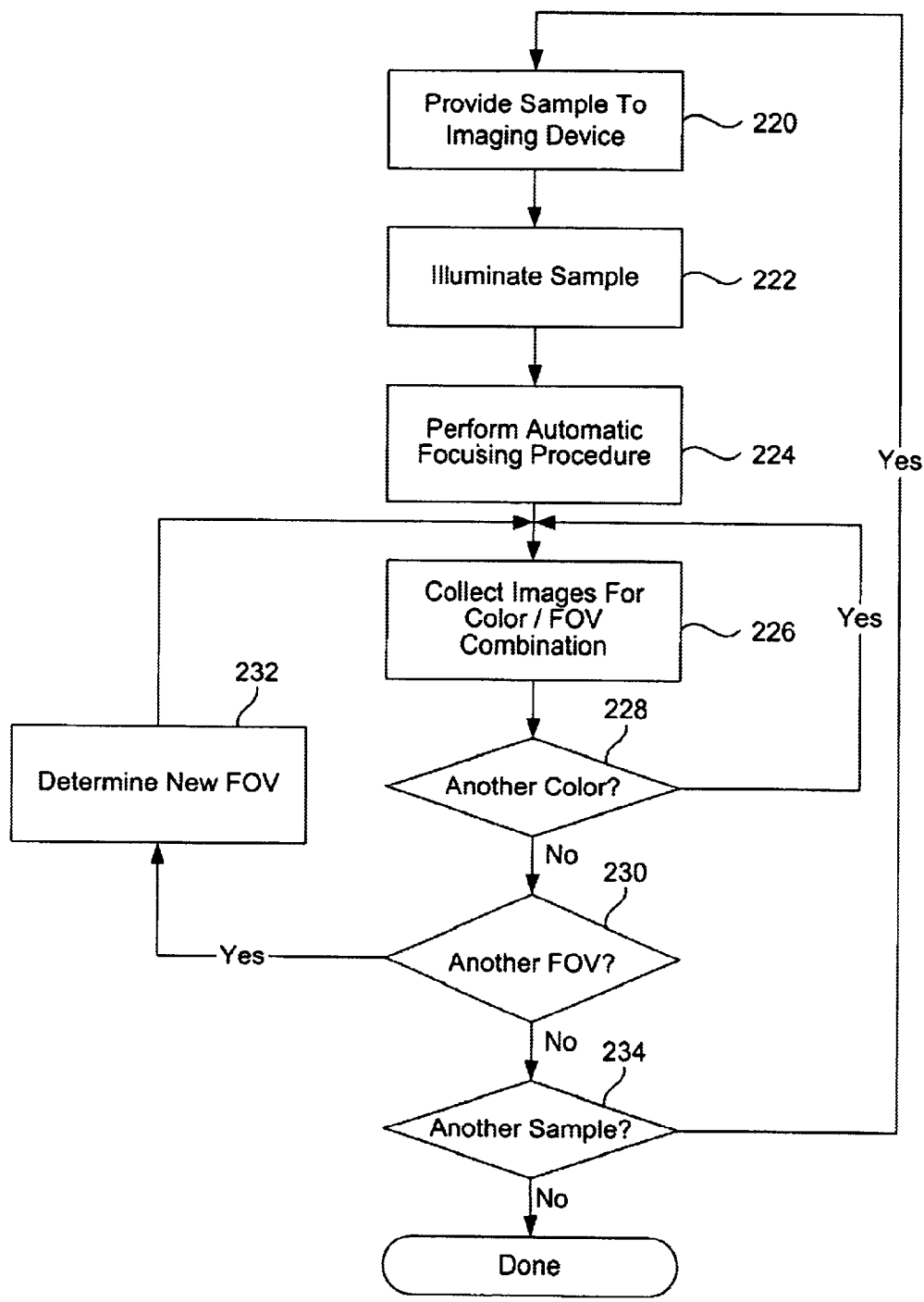

FIG. 2C illustrates a representative block flow diagram of simplified process steps for obtaining images of cell components of step 212 of FIG. 2B in a particular embodiment according to the present invention. This diagram is merely an illustration and should not limit the scope of the claims herein. One of ordinary skill in the art would recognize other variations, modifications, and alternatives. FIG. 2C illustrates a step 220, of providing a sample to the imaging device. Samples can be provided in 96 well plates and the like. The sample may be loaded into a microscope, such as a Zeiss microscope or equivalent. In a step 222, a light is used to illuminate the first sample, which may be contained in a first well designated A1. Then, in a step 224, an automatic focusing procedure is performed for the site. In a particular embodiment, the plate holding the samples is moved to perform automatic focusing of the microscope. In an alternative embodiments, focusing can be performed by moving optical components of the microscope and the like. In a step 226, images are collected for the site. Images can be collected for every color at every site. Present embodiments can provide images for up to four colors. However, embodiments are contemplated that can provide more colors by using either a monochromator or by digitally separating overlapping fluorophores. Cell growth and density information is collected. In some embodiments, imaging can be facilitated using one or more biosensors, molecules such as non-proteins, i.e., lipids and the like, that are luminescently tagged. However, some embodiments can also use fluorescence polarization and the like. Further, embodiments can detect differences in spectral shifts of luminescent markers. In a step 228, a determination is made whether more images need to be taken for a particular color. If this is so, then processing continues at step 226 with a different color. Otherwise, processing continues with a decisional step 230. Images can now be taken by repeating step 226. In a step 230, a determination is made whether more images need to be taken in order to obtain images for all fields of view for the sample. If this is so, then in a step 232 a field of view is determined and the sample is moved to this new field of view. Images for the new field of view can now be taken by repeating step 226. Then, in a decisional step 234, after images for fields of view in a sample have been obtained, a determination is made whether any further samples remain to be analyzed. If so, a new sample is brought into view and processing continues with step 220. Otherwise, image processing is complete and data analysis is performed on the images. In a presently preferable embodiment, image data can be stored on a CD ROM using a CD ROM burner, removable storage units, such as ZIP drives made by IOMEGA, and the like. However, other mass storage media can also be used.

Figure 2D:
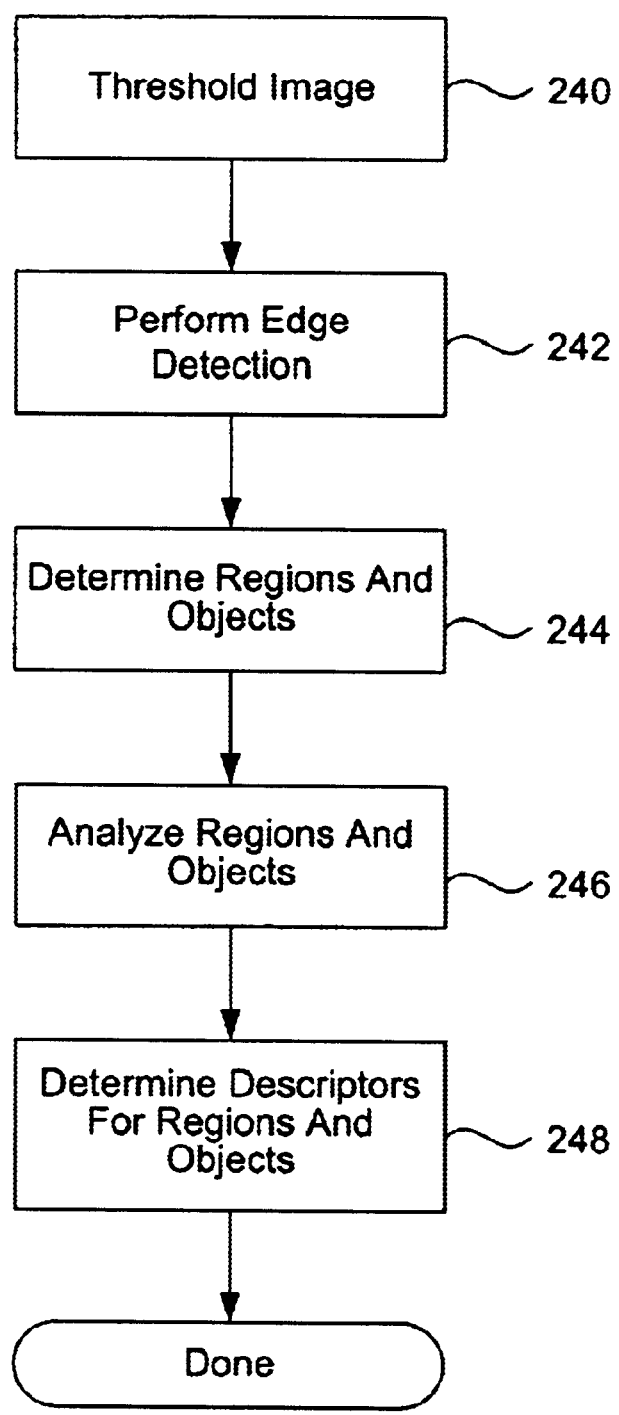

FIG. 2D illustrates a representative block flow diagram of simplified process steps for processing digitized representations of step 216 of FIG. 2B in a particular embodiment according to the present invention. This diagram is merely an illustration and should not limit the scope of the claims herein. One of ordinary skill in the art would recognize other variations, modifications, and alternatives. FIG. 2D illustrates a step 240, of thresholding a digitized image input. Thresholding provides a specific intensity level, such that pixels darker than the threshold are deemed black, and pixels lighter than the threshold are considered white. The resulting image can be processed using binary image processing techniques in order to extract regions. Then, in a step 242, the digitized image input is subjected to edge detection. Edge detection can be accomplished by means of passing a Sobol operator over the entire image and computing new pixel values based upon the contents of the Sobol operator and the original image. However, embodiments can also use other techniques, such as Fast Fourier Transforms (FFT) and the like as known in the art without departing from the scope of the present invention. Then, in a step 244, the regions and objects determined by step 240 and step 242 can be determined based upon image processing techniques.

In a step 246, the regions and objects determined by step 244 can be processed in view of a plurality of classification heuristics to determine cell state based upon selectable criteria. Further, in some embodiments, morphological criteria can be used based upon a cell type to determine cell state. Next, in a step 248, a plurality of region features can be determined. For example, in a representative embodiment, image features can include such quantities as area, perimeter, dimensions, intensity, gray level, aspect ratios, and the like.

In a particular embodiment according to the present invention, data analysis techniques for describing the fluorescence patterns of markers in multiple cell lines in the presence and absence of compounds are provided. Automated image analysis techniques can include determining one or more regions from around nuclei, individual cells, organelles, and the like, called "objects" using a thresholding function. Objects that reside on the edge of an image can be included or excluded in various embodiments. An average population information about an object can be determined and recorded into a database, which can comprise an Excel spreadsheet, for example. However, embodiments can use any recording means without departing from the scope of the present invention. Values measured can be compared to the visual image. One or more types of numerical descriptors can be generated from the values. For example, descriptors such as a Number of objects, an Average, a standard deviation of objects, a Histogram (number or percentage of objects per bin, average, standard deviation), and the like can be determined.

In a particular embodiment according to the present invention, data can be analyzed using morphometric values derived from any of a plurality of techniques commonly known in the art. Fluorescent images can be described by numerical values, such as for example, an area, a fluorescence intensity, a population count, a radial dispersion, a perimeter, a length, and the like. Further, other values can be derived from such measurements. For example, a shape factor can be derived according to a relationship $4\pi*area/perimeter$. Other values can be used in various embodiments according to the present invention. Such values can be analyzed as average values and frequency distributions from a population of individual cells.

In a particular embodiment according to the present invention, techniques for the automatic identification of mitotic cells are provided. Image analysis techniques employing techniques such as multidimensional representations, frequency-based representations, multidimensional cluster analysis techniques and the like can be included in various embodiments without departing from the scope of the present invention. Techniques for performing such analyses are known in the art and include those embodied in MatLab software, produced by Math Works, a company with headquarters in Natick, Mass.

Scalar values providing efficacious descriptors of cell images can be identified using the techniques of the present invention to perform predictive analysis of drug behavior. In a presently preferred embodiment, a plurality of heterogenous scalar values can be combined to provide predictive information about substance and cell interactions.

Figure 2E:
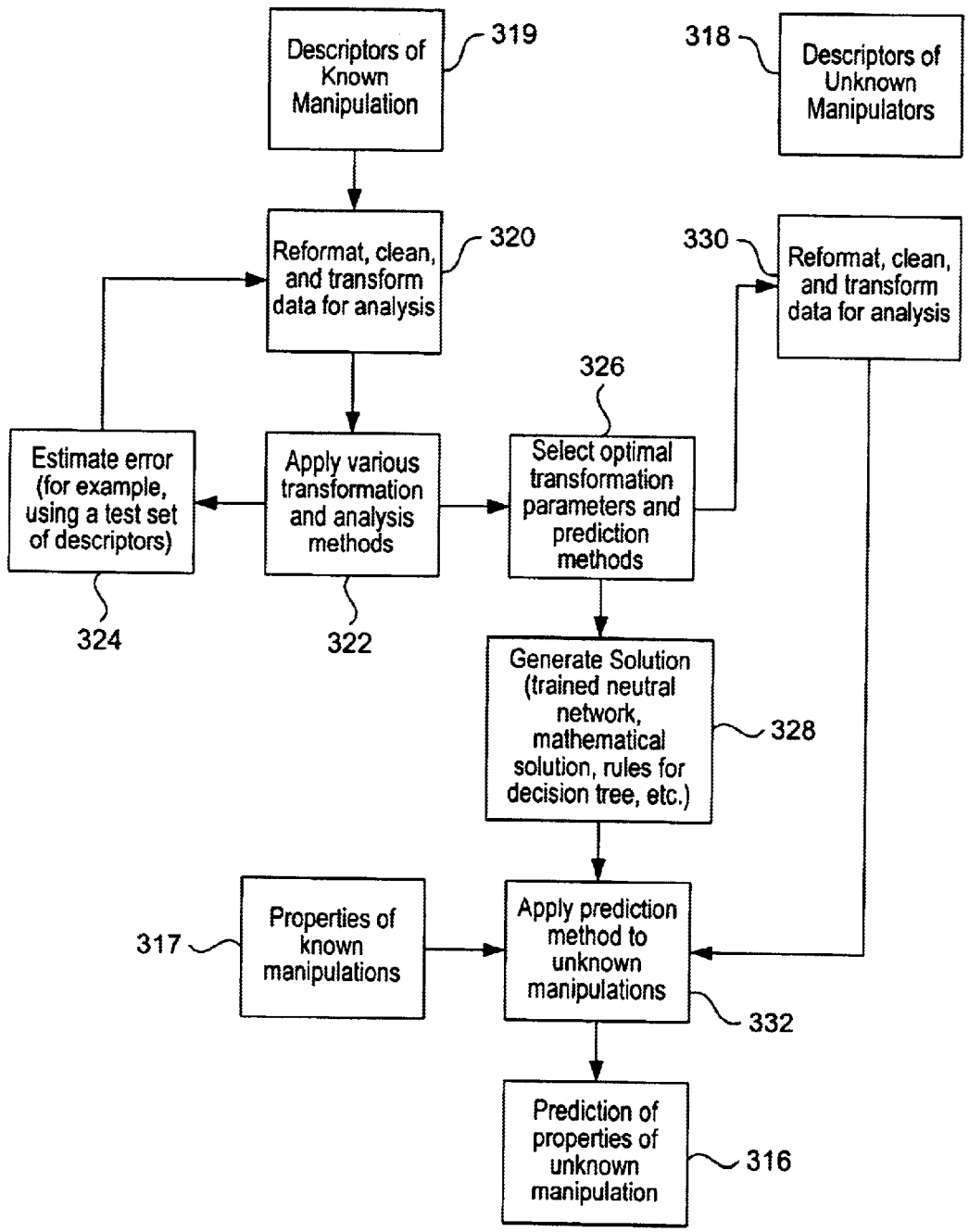

FIG. 2E illustrates a representative work flow diagram of simplified process steps for designing and applying analysis techniques for prediction of properties of manipulations in a particular embodiment according to the present invention. This diagram is merely an illustration and should not limit the scope of claims herein. One of ordinary skill in the art would recognize other variations, modifications, and alternatives. FIG. 2E illustrates an input data of descriptors of known manipulations with known properties. A step 320 of reformatting and transforming data 319 to formats suitable for analysis is performed. Additionally, a "cleaning", or "cleansing" step can eliminate outlying and/or incomplete data points and the like in the data. Than at step 322 a set of models is being built based on data from step 320. Performance of each of these models is evaluated at step 324 and steps 320, 322, and 324 are repeated until a desired performance and error rates are achieved. Data transformations and prediction methods, including a particular neural network, mathematical equation, classification and decision trees and/or the like, that satisfy these criteria are selected at step 326 and a solution based on these transformations and methods is generated at step 328. Formatting and transformations, based upon procedures and parameters selected in step 326, are applied to descriptors of unknown manipulations 318 at step 330. Reformatted and transformed data from step 330 is analyzed using a generated solution 328, and predictions about unknown manipulations are generated at step 316, based on this analysis (332) and known properties of know manipulations 317.

Figure 2F:
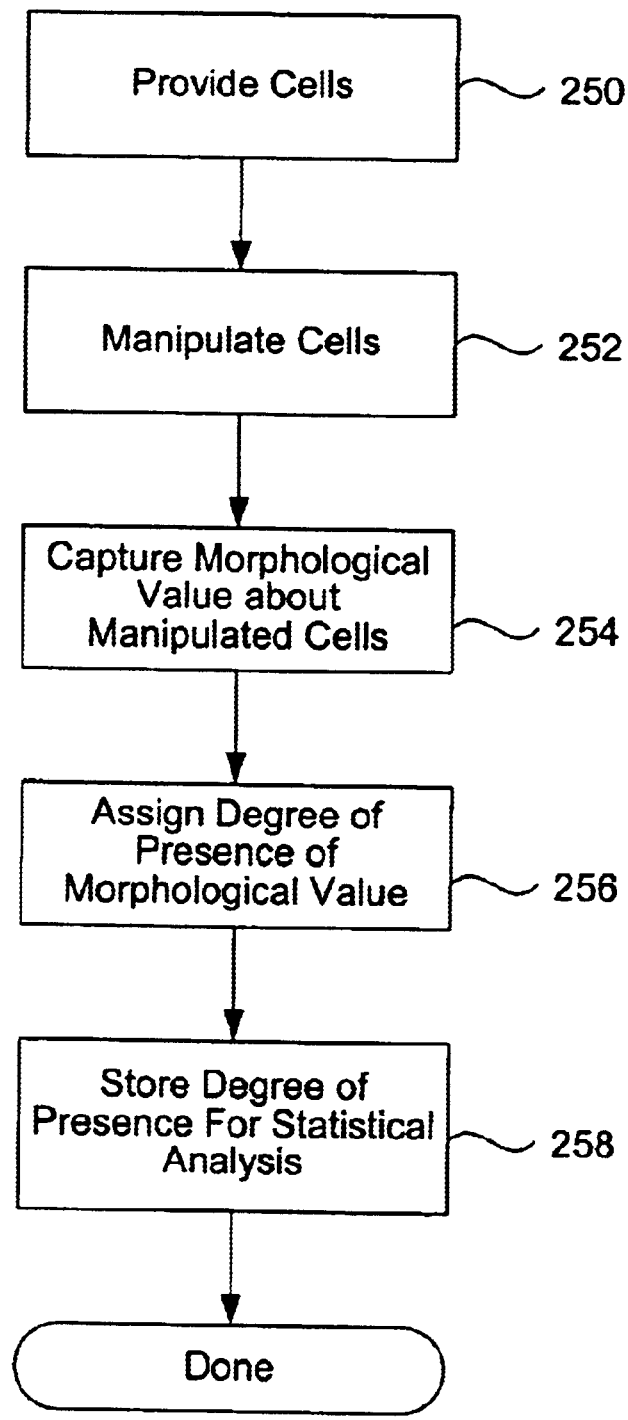

FIG. 2F illustrates a representative block flow diagram of simplified process steps for a method of mapping a manipulation of cells to a morphological characteristic in a particular embodiment according to the present invention. This diagram is merely an illustration and should not limit the scope of the claims herein. One of ordinary skill in the art would recognize other variations, modifications, and alternatives. FIG. 2F illustrates a step 250, wherein a plurality of cells, e.g., living cells, fixed cells or dead cell fractions, cell substructures, cell components are provided. Then, in a step 252, the plurality of cells is manipulated, where manipulation occurs using a source(s) from one or a combination selected from an electrical source, a chemical source, a thermal source, a gravitational source, a nuclear source, a temporal source, and a biological source. Next, in a step 254, a morphological value is captured from the plurality of cells. The morphological value can include one or any combination of characteristics such as a cell count, an area, a perimeter, a length, a breadth, a fiber length, a fiber breadth, a shape factor, an elliptical form factor, an inner radius, an outer radius, a mean radius, an equivalent radius, an equivalent sphere volume, an equivalent prolate volume, an equivalent oblate volume, an equivalent sphere surface area, an average gray value, a total gray value, and an optical density. Then, in a step 256, a degree of presence of the morphological value is assigned. In a step 258, the morphological value from the plurality of cells is stored in a memory location. From the memory location the values can be used for a statistical analysis to produce a statistical profile.

Figure 2G:
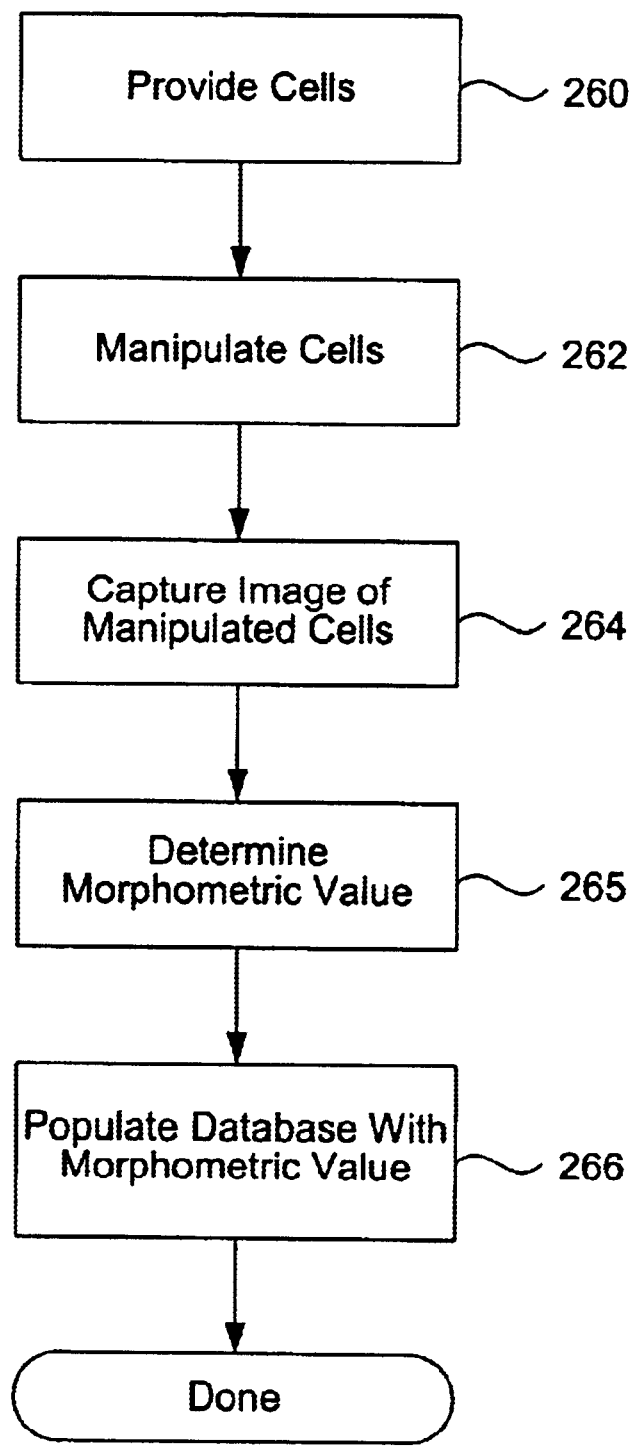

FIG. 2G illustrates a representative block flow diagram of simplified process steps for populating a database with manipulated biological information, e.g., cellular enzymatic activities, cellular cascades, cellular promoters, transcription factors, translation factors, cell cycle stage and apoptosis, in a particular embodiment according to the present invention. This diagram is merely an illustration and should not limit the scope of the claims herein. One of ordinary skill in the art would recognize other variations, modifications, and alternatives. FIG. 2G illustrates a step 260, wherein a plurality of cells in various stages of the cell cycle, such as for example, interphase, G0 phase, G1 phase, S phase, G2 phase, M phase, which itself includes prophase, prometaphase, metaphase, anaphase, and telophase, are provided. Then, in a step 262, each of the cells in the various stages of the cell cycle is manipulated. Next, in a step 264, an image of the plurality of manipulated cells is captured using image acquisition techniques in order to provide a morphometric value for the manipulated cells. Finally, in a step 266, a database is populated with the morphometric value. The database can later be queried based upon the morphometric value.

Figure 2H:
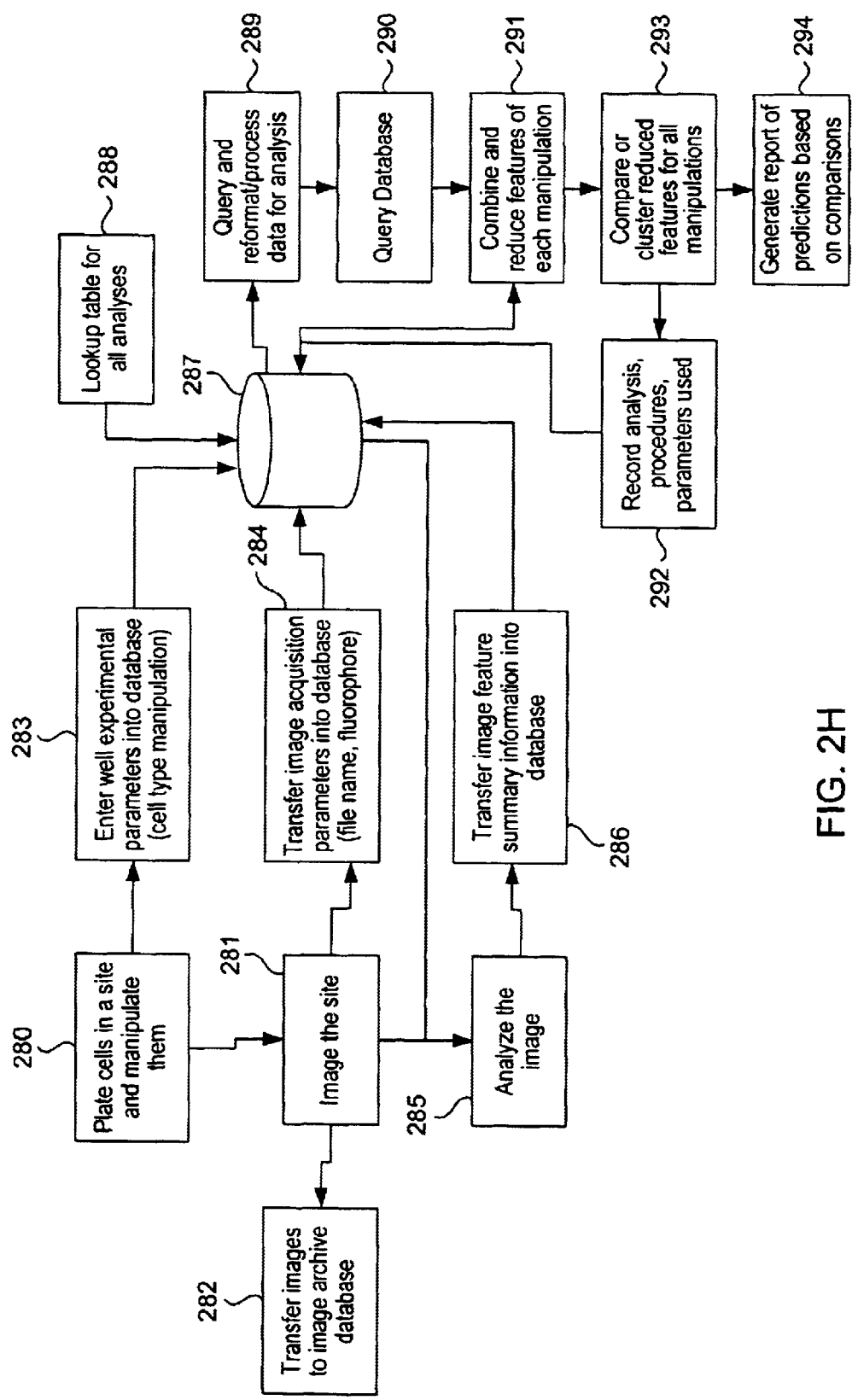
Figure 21:
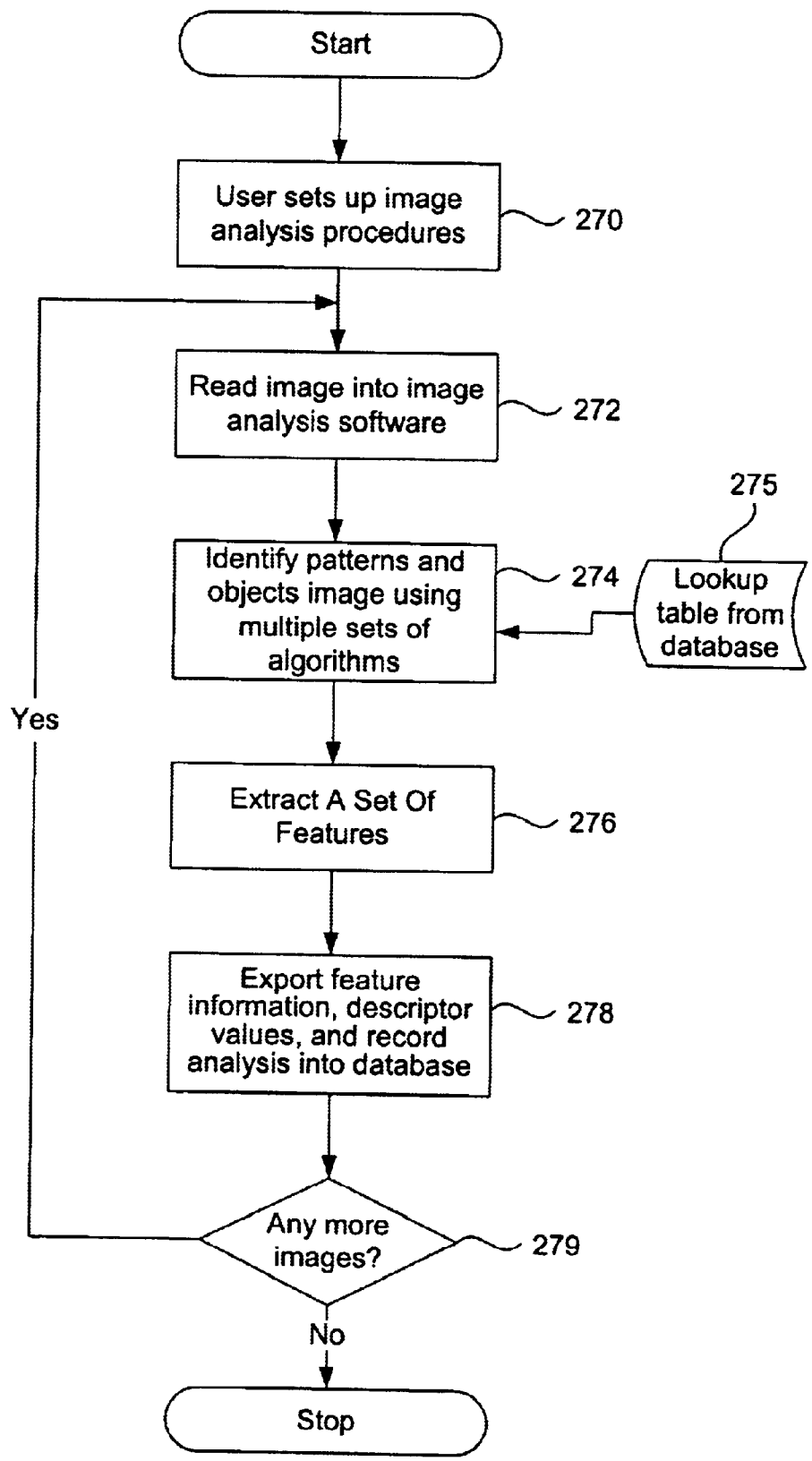

FIG. 2H illustrates a representative block flow diagram of simplified process steps for a method for populating a database with manipulated biological information, e.g., image acquisition parameters, image feature summary information, and well experimental parameters in a particular embodiment according to the present invention. This diagram is merely an illustration and should not limit the scope of the claims herein. One of ordinary skill in the art would recognize other variations, modifications, and alternatives. FIG. 2H illustrates a step 280 in which cells are placed into site on a plate and a manipulation is applied. Then, in a step 281 an image is taken of the cells. In step 282, the image is transferred to an image archive database. Then, in a step 283, well experimental parameters are entered into the database 287. Well experimental parameters can include cell type, manipulation and the like. In a step 284, image acquisition parameters are transferred to database 287. Image acquisition parameters can include file name, fluorophores and the like. In a step 285, the image acquired in step 281 is analyzed. Then, in step 286, an image feature summary from the analysis step 285 is transferred to database 287.

In step 288, a lookup table for all analyses is provided to database 287. The lookup table provides information about the analyses. In a step 289, a query of database 287 for process data is performed. The results are reformatted. Then in a step 290, the database 287 is queried. Next, in a step 291, features of the manipulations stored in the database are combined and reduced. Next, in a step 293, reduced features of step 291 can be compared. In a step 292, the results of step 293 are recorded in database 287. Then, in a step 294, a report of predictions based on comparisons performed in step 293 is generated.

FIG. 2I illustrates a representative block flow diagram of simplified process steps for acquiring images of manipulated biological information, e.g., cells, cell tissues, and cell substituents in a particular embodiment according to the present invention. This diagram is merely an illustration and should not limit the scope of the claims herein. One of ordinary skill in the art would recognize other variations, modifications, and alternatives. FIG. 2I illustrates a step 270 in which a user sets up an image analysis procedure. Then, in a step 272, an image is read into image analysis software. Next, in a step 274, patterns and objects are identified in the image using one or more algorithms. Next, in a step 276, sets of features are extracted from the image. Then, in a step 278, feature information, descriptor values and the like are exported to the database, such as database 287 of FIG. 2H, for recording. Next, in a decisional step 279, a determination is made whether any more images should be taken. If this is so, processing continues with step 272. Otherwise, image acquisition processing is completed.

Figure 2J:
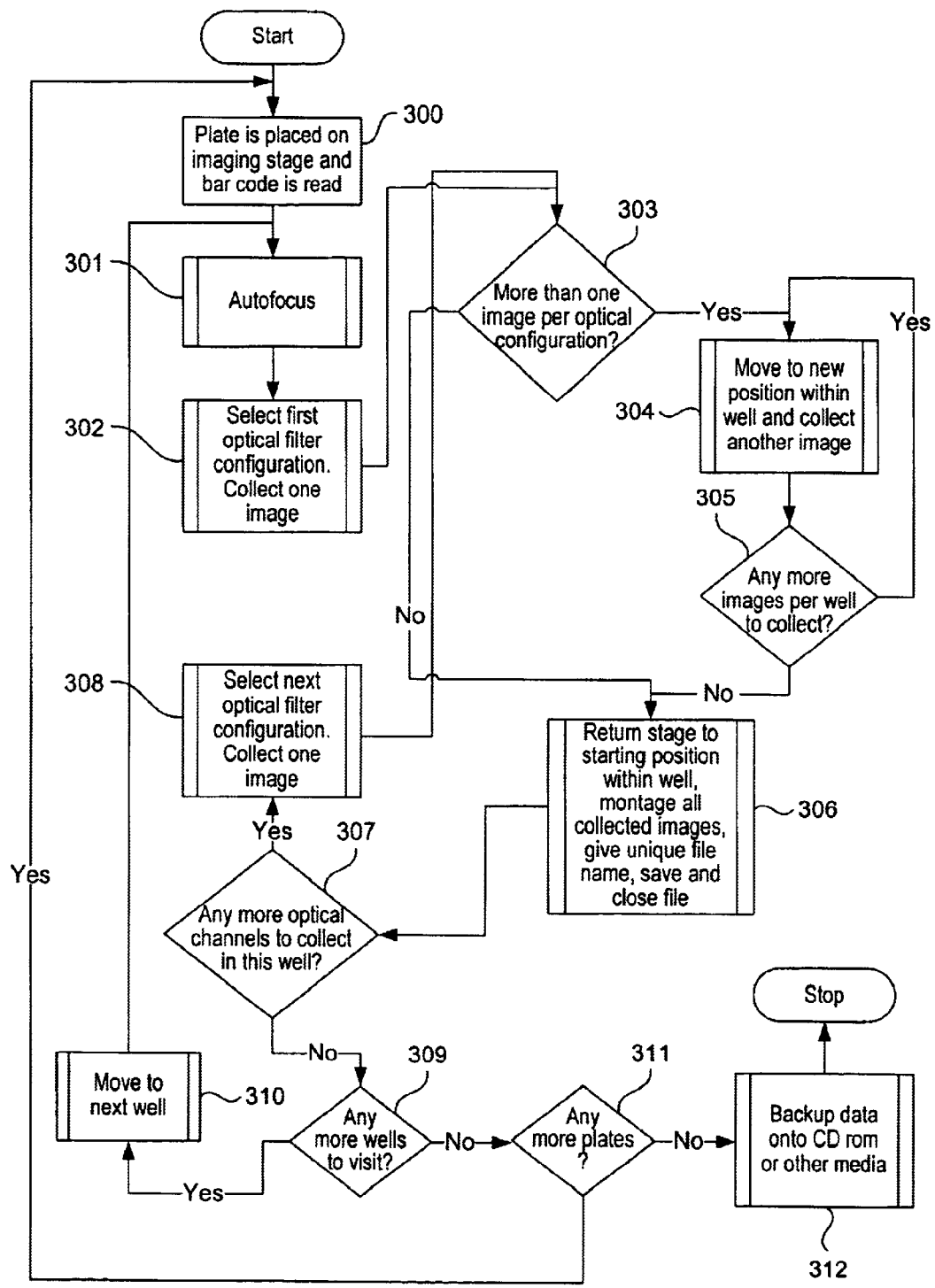

FIG. 2J illustrates a representative block flow diagram of simplified process steps for populating, acquiring and analyzing images of manipulated biological information in a particular embodiment according to the present invention. This diagram is merely an illustration and should not limit the scope of the claims herein. One of ordinary skill in the art would recognize other variations, modifications, and alternatives. FIG. 2J illustrates a step 300 of placing a plate onto an imaging stage and reading a bar code. Then, in a step 301 an autofocus procedure is performed. Next, in a step 302, a first optical filter configuration is selected and an image is collected. Then, in a decisional step 303, a determination is made whether more than one image per optical configuration can be taken. If so, then, in a step 304, a new position within the well is targeted and another image is collected. Then, in a decisional step 305, a determination is made whether any more images need to be collected. If this is so, step 304 is repeated until all images for a particular well have been collected. After one or more images are collected for the well, in a step 306, the stage is returned to a starting position within the well, and a montage is created from collected images. The results are named with a unique file name and stored.

In a decisional step 307, a determination is made whether any more optical channels in the well can be imaged. If this is so, then in a step 308 the next optical filter configuration is selected and an image is collected. Processing then continues with decisional step 303, as described above. Otherwise, if no further optical channels in the well can be imaged, then in a decisional step 309 a determination is made whether any wells remain to be imaged. If not all wells have been imaged, then in a step 310, the stage moves to the next well and processing continues with step 301, as described above. Otherwise, if all wells on the plate have been imaged, then in a decisional step 311, a determination is made whether any more plates can be processed. If this is so, then processing continues with step 300 as described above. Otherwise, in a step 312, the information is stored to a CD or other storage device as a backup.

Figure 2K:
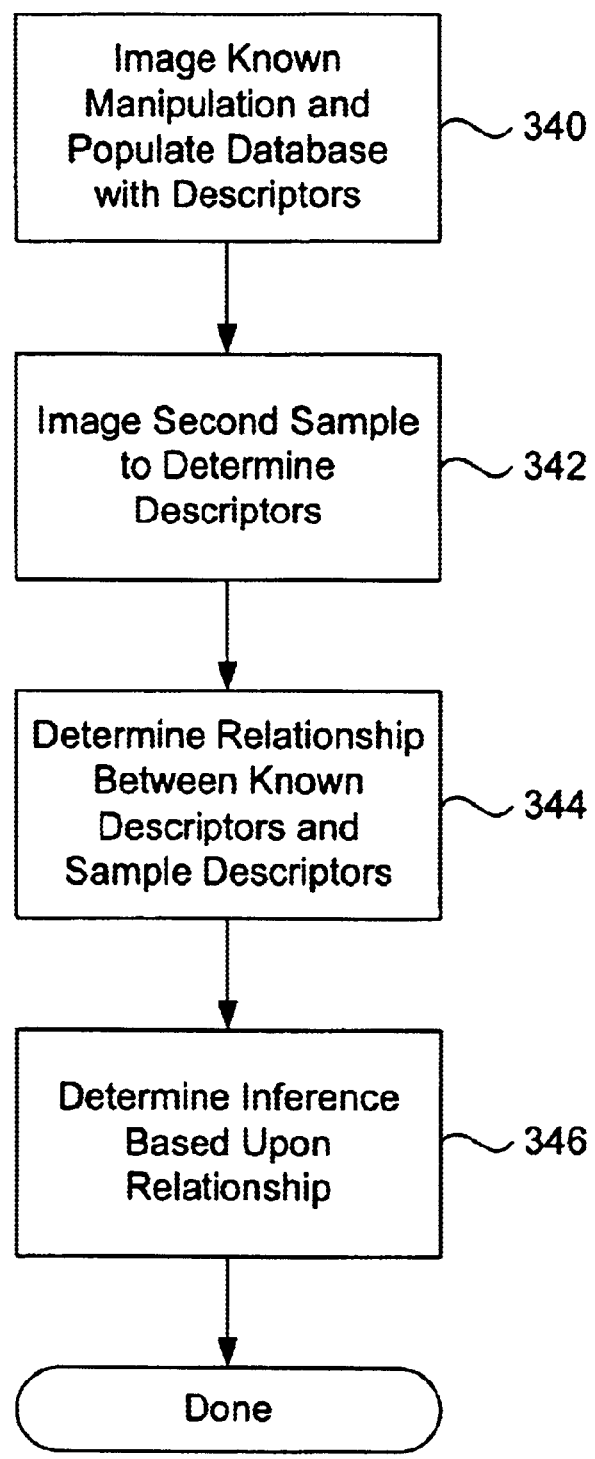

FIG. 2K illustrates a representative block flow diagram of simplified process steps compound based upon information about effects of one or more known compounds on a cell population in a particular embodiment according to the present invention. This diagram is merely an illustration and should not limit the scope of the claims herein. One of ordinary skill in the art would recognize other variations, modifications, and alternatives. FIG. 2K illustrates a step 340 of populating a database with descriptors for known compounds. Such descriptors can be determined from imaging the cell population. However, in some embodiments, descriptors can be derived by measurements and combinations of measurements and the like. Then, in a step 342, descriptors for the unknown compound are determined from imaging a second cell population. The second cell population has been treated with the unknown compound. Then, in a step 344, a relationship between the descriptors determined from the unknown compound with the descriptors determined from the known compounds can be determined. Finally, in a step 346, an inference can be made about the unknown compound based upon the descriptors of the known compounds from the relationship determined in step 344.

Accordingly, the present invention provides a novel database design. In a particular embodiment according to the present invention, a method for providing a database comprises measurement of a potentially large number of characteristics of one or more sub-cellular morphometric markers. Markers can be from any of a large variety of normal and transformed cell lines from sources such as for example, human beings, fungi, or other species. The markers can be chosen to cover many areas of cell biology, such as, for example markers comprising the cytoskeleton of a cell. The cytoskeleton is one of a plurality of components that determine a cell's architecture, or "cytoarchitecture". A cytoarchitecture comprises structures that can mediate most cellular processes, such as cell growth and division, for example. Because the cytoskeleton is a dynamic structure, it provides a constant indication of the processes occurring within the cell. The cytoarchitecture of a cell can be quantified to produce a one or more scalar values corresponding to many possible cellular markers, such as cytoskeleton, organelles, signaling molecules, adhesion molecules and the like. Such quantification can be performed in the presence and absence of drugs, peptides, proteins, anti-sense oligonucleotides, antibodies, genetic alterations and the like. Scalar values obtained from such quantification can provide information about the ongoing cell biological function and physiologic state of the cell.

In a presently preferred embodiment, scalar values can comprise morphometric, frequency, multi-dimensional parameters and the like, extracted from one or more fluorescence images taken from a number of cellular markers from a population of cells. A vector of two or more such scalar values extracted from a plurality of cell lines and markers grown in the same condition together comprise a unique "fingerprint" that can be incorporated into a database. Such cellular fingerprints will change in the presence of drugs, peptides, proteins, antisense oligonucleotides, antibodies or genetic alterations. Such changes can be sufficiently unique to permit a correlation to be drawn between similar fingerprints. Such correlations can predict similar behaviors or characteristics with regard to mechanism of action, toxicity, animal model effectiveness, clinical trial effectiveness, patient responses and the like. In a presently preferred embodiment, a database can be built from a plurality of such fingerprints from different cell lines, cellular markers, and compounds having known mechanisms of action (or structure, or gene response, or toxicity).

The present invention also provides database and finger print comparisons according to other embodiments. In a particular embodiment according to the present invention, measurement of scalar values can provide predictive information. A database can be provided having one or more "cellular fingerprints" comprised of descriptors of cell substance interactions of drugs having known mechanisms of action with cells. Such fingerprints can be compared using a plurality of techniques, such as a technique of creating "phylogenetic trees" of a statistical similarity between the cellular fingerprints from various drugs. In a present embodiment, scalar, numeric values can be converted into a nucleotide or amino acid letter. Once converted into a corresponding nucleotide representation, the fingerprints can be analyzed and compared using software and algorithms known in the art for genetic and peptide sequence comparisons, such as GCG, a product of Genetics Computer Group, with company headquarters in Madison Wis. In an alternative embodiment, numeric values for the fingerprints can be used by comparison techniques. A phylogenetic tree can be created that illustrates a statistical significance of the similarity between fingerprints for the drugs in the database. Because the drugs used to build the initial database are of known mechanism, it can be determined whether a particular scalar value in a fingerprint is statistically predictive. Finally, a compound fingerprint with no known mechanism of action can be queried against the database and be statistically compared and classified among the drugs in the database that the compound most resembles.

In a particular embodiment, relationships between measured morphological properties of images and physiological conditions can be determined. Relationships can include, for example, treatment of different cell lines with chemical compounds, or comparing cells from a patient with control cells, and the like. In a presently preferable embodiment, a clustering can be performed on acquired image feature vectors. Some embodiments can comprise statistical and neural network—based approaches to perform clustering and fingerprinting of various features. The foregoing is provided as merely an example, and is not intended to limit the scope of the present invention. Other techniques can be included for different types of data.

In some embodiments, clustering and fingerprinting can be performed on features extracted from cell images. In a presently preferable embodiment, procedures for comparisons and phylogenetic analysis of biological sequences can be applied to data obtained from imaging cells.

Embodiments can perform such analysis based upon factors such as numerical value, statistical properties, relationships with other values, and the like. In a particular embodiment, numbers in a numerical features vector can be substituted by one or more of nucleic acid or amino acid codes. Resulting "pseudo-sequences" can be subjected to analysis by a sequence comparison and clustering program.

Other types of databases can also be provided according to other embodiments. The database includes details about the behavior of a plurality of standard drugs of known mechanism in the universal assay, called a morphometric cellular response. However, the comparative value need not be limited to drugs having a known mechanism of action. When the profile of a test compound is compared to the database, predictions about the test compound can be made against any known parameter of the other compounds in the database. For example, information about a compound in the database could include structure, mechanism of action, clinical side effects, toxicity, specificity, gene expression, affinity, kinetics, and the like. The fingerprint of a compound of unknown structure from a natural products library could be compared to the fingerprint of drugs with known structure and the structure could be deduced from such a comparison. Similarly, such information could lead to better approaches to compound analoging, pre-clinical animal modeling, clinical trial design (side effects, dose escalation, patient population) and the like.

According to the present invention, databases can be integrated with and complementary to existing genomic databases. Differential genomic expression strategies can be used for drug discovery using database technology. In one particular embodiment, cell data and morphometric cellular response data can be associated with a genetic expression profile assay to form a single assay. Live cells expressing fluorescence markers can be treated with a drug, imaged and analyzed for morphometry; and then analyzed for mRNA for expression. Such embodiments can provide rapid development of tools to link cellular behavior with genomics.

Database methods according to the present invention can be used to predict gene function and to assist in target validation. Databases that include genetic diversity, i.e., having cellular fingerprints from cells of differing genetic backgrounds (tumor, tissue specific, and gene knock out cell lines), can provide the capability to compare cells of unknown genetic background to those in the database. Similarly, fluorescent patterns of an unknown cellular marker in the presence of multiple drugs can be queried against the patterns of the known markers in the database. For example, if an unknown gene is tagged with Green Fluorescent Protein (GFP), the database may be used to identify the cellular structures for which that unknown gene encodes.

According to the present invention, target validation and cell-based assay screening can be performed using database system and methods to serve as a universal high-throughput cell-based assay that can evaluate the molecular mechanism of drug action. As new genes are isolated and identified, a large collection of available gene based knowledge is becoming available. From this large collection of new genes, potential targets can be identified using the genomic tools of sequence analysis and expression profiling. However, unless a gene mutation is tightly linked to a disease state, further validation of individual targets is a time consuming process, becoming a bottleneck in drug discovery. Furthermore, robotics and miniaturization are making "High Throughput Screening (HTS)" the industry standard, substantially reducing the time and cost of running a target-based biochemical assay. Therefore, it is now be possible to routinely screen large libraries and use a resulting "hit" to validate the target. In such approaches, a specialized cell-based assay would be developed to test hits for each target. Since this often involves the creation of cell lines expressing new markers, this stage may also become a bottleneck that cannot keep pace with HTS. In addition, these assays may not be amenable to high-throughput screening, making it difficult to test the increasing number of analogs arising from combinatorial chemistry.

In a particular embodiment according to the invention, a rapid characterization of large compound libraries for potential use as pharmaceutical products can be provided by predicting compound properties such as mechanisms of action. In many drug discovery situations, virtually millions of compounds can be passed through an HTS assay against one or two validated targets. These assays produce hundreds to thousands of potential hits that can be narrowed down to a selective few. These hits can then be subsequently screened by a pipeline of secondary and tertiary screens to further characterize their specificity, often time completely missing non-specific interactions with other proteins. Techniques according to the present invention can provide a replacement to such screening operations by providing information about cellular accessibility and mechanism of action for the substances usually placed on HTS systems. The cell information can be predictive of whether to continue into an animal model for each compound, and which animal model to pursue.

In some embodiments, techniques according to the present invention can provide tools for the later stages of drug development such as clinical trial design and patient management. The predictive value of the known drug trial and patient response information will be used in a similar fashion as the pre-clinical information. Because the human cell is the locus of drug action, a database containing cellular interactions can be able to provide predictive value for this aspect of drug development.

EXPERIMENTS

To prove the principle and demonstrate the objects of the present invention, experiments have been performed to determine the effects of manipulations on cell structure based upon imaging techniques applied to a variety of indications. These experiments were performed by growing multiple cell lines in the presence of multiple compounds, or substances. A fix and stain of cells using antibodies or labels to multiple cellular markers was performed. One or more images of the cells were then obtained using a digital camera. Indications were built by quantifying and/or qualifying patterns of each marker in the cell lines under study. A database was built from the indications.

As the database grows, it should be able to predict the mechanism of action and other compound properties of an unknown drug by comparing its effect with the effects of known compounds or to identify data clusters within large libraries of compounds.

In a first experiment, an automated method to count the number of cells and differentiate normal, mitotic, and apoptotic cells was created. Approximately 5,000 HeLa cells were plated per well in a 96 well plate and grown for 3.5 days. The cells were fixed with −20° MEOH for 5 minutes, washed with TBS for 15 minutes, and then incubated in 5 mg/ml Hoechst 33342 in TBS for 15 minutes. Then, 72 images were collected with a 40× objective and 75 ms exposure time.

The analysis was performed on objects that met a certain size criteria that was based on 1) measuring the size of objects in the image that were clearly not cells and 2) excluding the first peak of the area histogram.

Figure 3A:
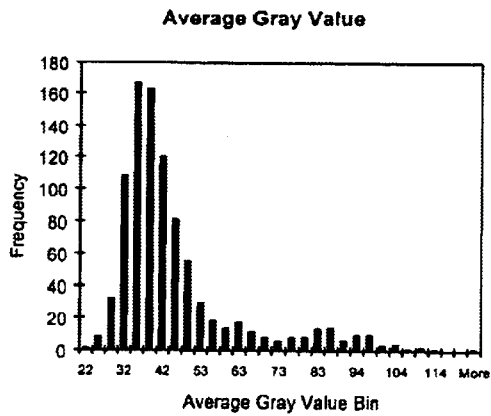
FIG. 3A–3F illustrate representative quantified descriptors of effects of manipulations on images of cells in a particular experiment.
Figure 3B:
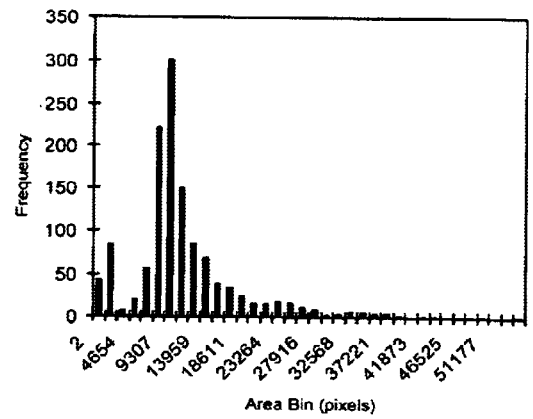
Figure 3C:
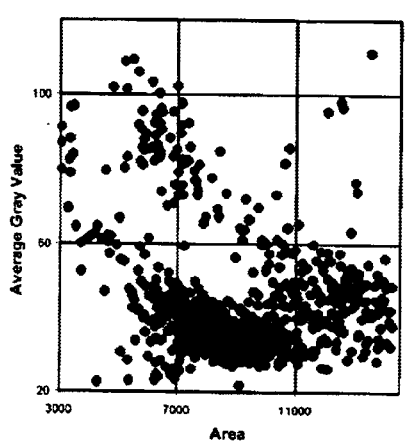
Figure 3D:
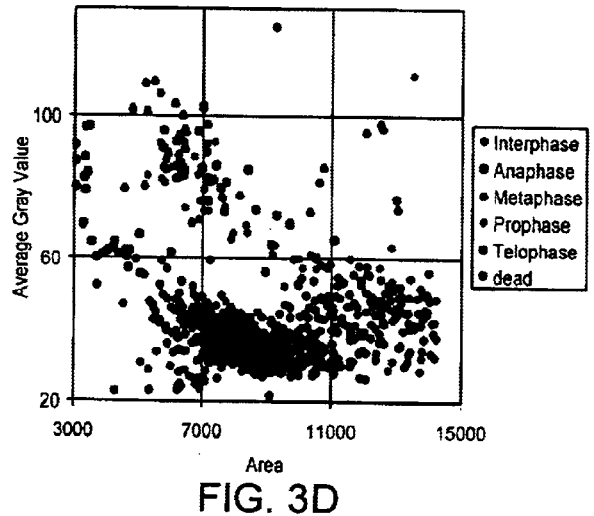
Figure 3E:
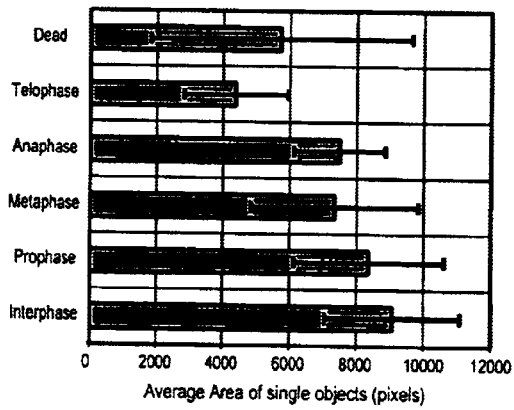
Figure 3F:
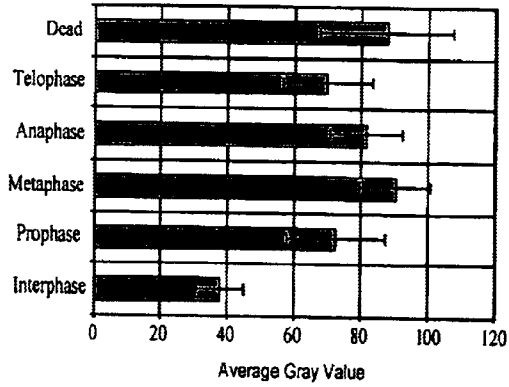

Histograms of the individual object data were generated for each type of information. FIG. 3A shows the histogram for average gray value, and FIG. 3B shows histogram data for the area of each object. FIG. 3C shows the scatter plot of the average gray value vs. the area of all of the objects. The pattern of the scatter plot showed an interesting pattern: a large cluster of cells in one region of the graph, with a scattering of object points in other regions. Because mitotic structures are identified as particularly bright objects, most likely due to the biological fact that the chromatin is condensed, it seemed reasonable to go back to the original Hoechst images and the identify the cells which were either undergoing mitosis, or otherwise looked abnormal. Manual inspection of 917 cells resulted in the classification of each object. FIG. 3D shows a graph where each type of cellular classification is delimited. This graph clearly shows that the mitotic nuclei are exclusively brighter than the interphase nuclei. Further, the different phases of the cell cycle can be separated using these two parameters. FIGS. 3E–3F show the bar graphs of the average and standard deviations of the areas and average gray values for each cell classification type. These graphs shows that interphase nuclei are statistically less bright than mitotic nuclei and that telophase nuclei are statistically smaller than other mitotic nuclei.

Each image was thresholded to a level of 20. A standard area value was set at 9500 pixels. Automated information gathering about all of the objects was done and collected into an Excel spreadsheet (for more information see, section on imaging system). The following information was recorded:

| Image Name | Average gray value |
| --- | --- |
| Object # | Total gray value |
| Area | Optical density |
| Standard area count | Radial dispersion |
| Perimeter | Texture Difference Moment |
| Fiber length | EFA Harmonic 2, Semi-Major Axis |
| Fiber breadth | EFA Harmonic 2, Semi-Minor Axis |
| Shape factor | EFA Harmonic 2, Semi-Major Axis Angle |
| E11. form factor | EFA Harmonic 2, Ellipse Area |
| Inner radius | EFA Harmonic 2, Axial Ratio |
| Outer radius | EFA Harmonic 3, Semi-Minor Axis |
| Mean radius | |

The following results were obtained:

1,250 objects were counted 201 of those objects has standard area counts >2 (area >19000 pixels)

195 objects had areas <6000 pixels 1529 objects estimated in total 1328 object areas are >6000 pixels The data was reduced to 917 objects that were 6000 <area <19000

For the 917 objects a scatter plot of area vs. average gray value and a histogram of the average gray value were generated.

116 objects that had average gray value intensities >60 were manually looked at to determine their morphology.

Of those 116 objects:
  6 were dead or indistinguishable
  4 were interphase
  30 were prophase
  32 were metaphase
  24 were anaphase
  20 were telophase (10 pairs)

12 prophase objects were missed because of gray scale cut off. (8 of those prophase cells had gray scale values >57, as did 7 interphase)

1 telophase object was missed because it was too small (<6000)

1 prophase object was missed because it was too big (>1900)

16 mitotic objects were missed because they were parts of objects with standard count >2.

In sum, out of 917 single objects, the analysis correctly identified 106 out of 130 mitotic objects, or (81% predictive, 91% of identified mitotics). Out of 917 single objects, the analysis incorrectly identified only 10 non-mitotics as mitotics (1% total, 8% of identified mitotics); 14 mitotics as interphase (1.4% total, 1% interphase).

The next step is to develop an automated classification system which will automatically assign values to each object using these or other measurement parameters.

In a second experiment, the effects of Taxol on MDCK cells and the different types of morphological effects were observed. A plurality of MDCK cells grown in 96 well plates were treated with Taxol for 4.5 hours at different concentrations (10 uM-1 pM). They were then fixed, labeled with Hoechst, and imaged.

This experiment used a labeling protocol comprising: MEOH fix at −20°, Wash in PBS, Block in PBS/BSA/Serum/Triton-X 100, Incubate with 5 μg/ml Hoechst 10 minutes, and Wash.

Figure 4:
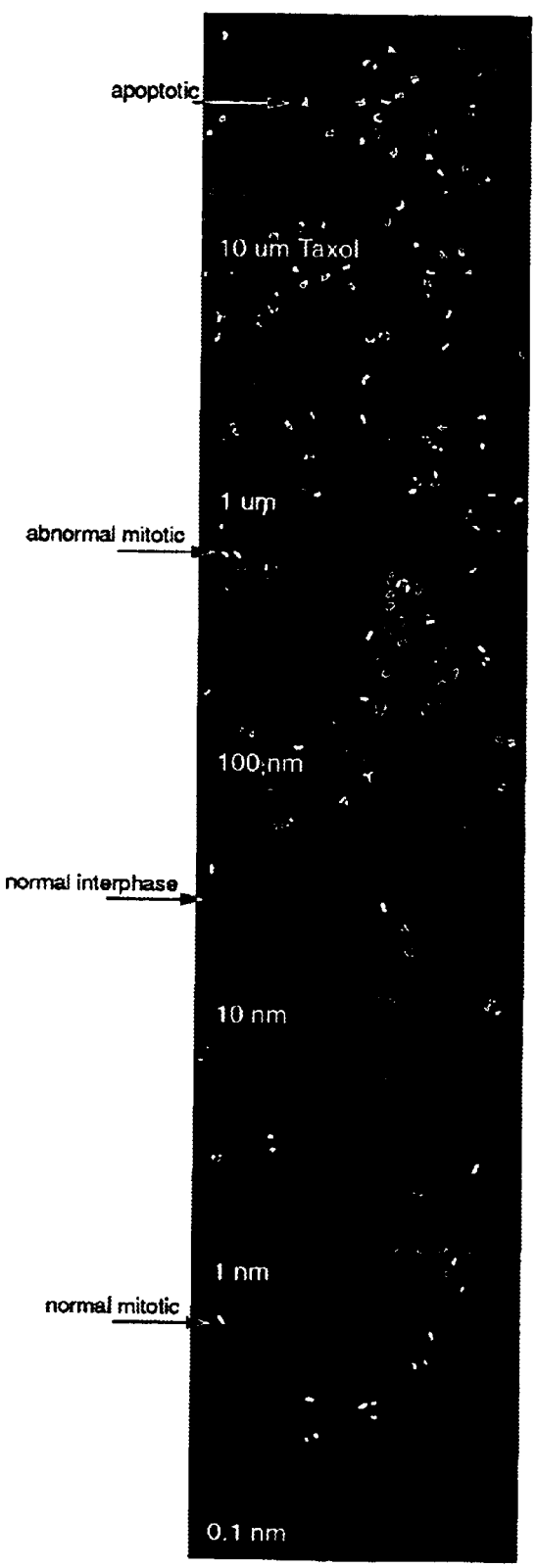
FIG. 4 illustrates example images for different types of morphologies in a particular experiment.
Figure 5:
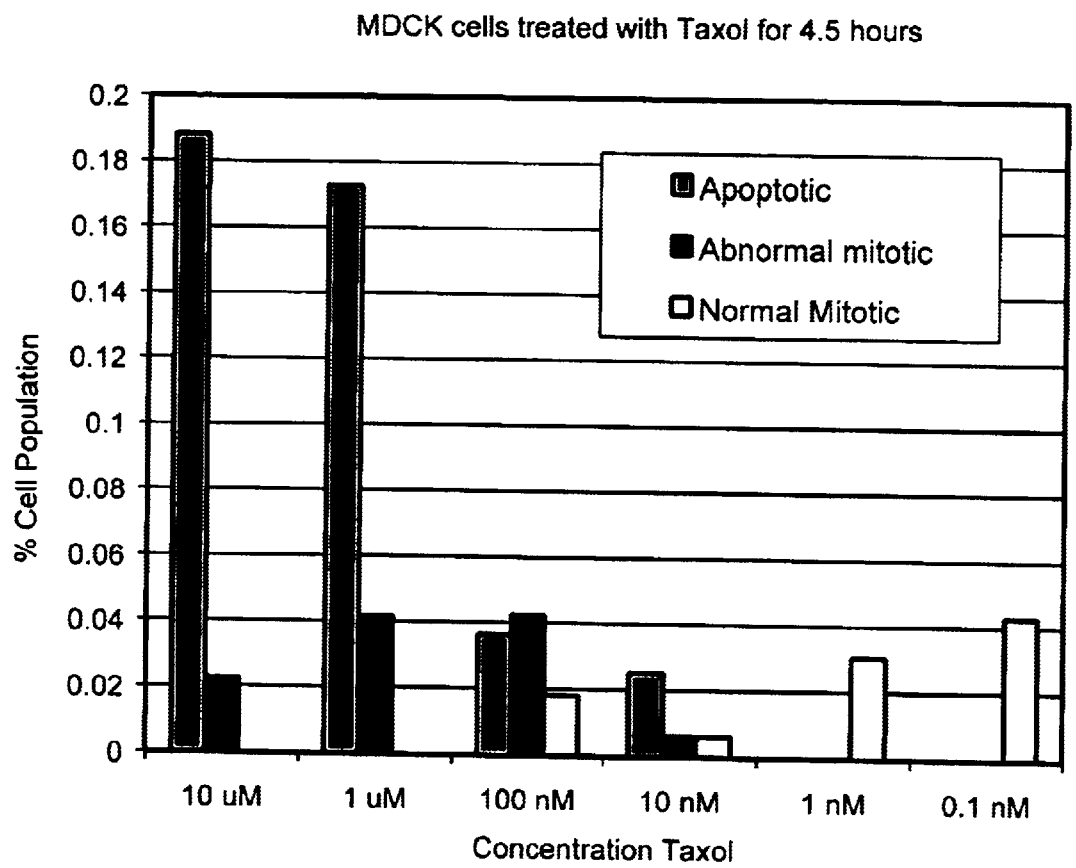
FIG. 5 illustrates a distribution of various morphologies in a cell population responsive to drug concentration in a particular experiment.

The results of the experiment are that cells were inspected for different morphologies and manually counted at each different drug concentration in one well. FIG. 4 shows example images from each drug concentration and the different types of morphologies are highlighted. FIG. 5 shows the distribution of each morphology within the cell population as a function of drug concentration. The higher the concentration of Taxol, the larger proportion of cells underwent apoptosis, and the fewer number of normal mitotic cells were detected.

The next step is to test the automated Hoechst analysis of the first experiment with multiple drugs.

In a third experiment, the purpose is to determine whether the automated analysis methods developed in the first experiment can detect differences in Hoechst morphology in the presence of 6 known compounds at one concentration and exposure time in one cell line. In this experiment, HeLa cells were treated with 6 compounds with known mechanism of action. The quantitative methods described in the first experiment were applied to the Hoechst images.

Approximately 5,000 HeLa cells per well were plated in a Costar black walled 96 well tissue culture treated plate and left to recover in the incubator for 24 hours. After this time, 10 ug/mL of cytochalasin D (CD), Taxol, hydroxyurea, vinblastine, and nocodazole, and staurosporine was added to different wells at a 1:100 addition in DMSO. The cells were incubated in the presence of drug for 24 more hours. After 24 hours, the cells were removed and fixed as in the first experiment. Then, 9 images per well were collected of the Hoechst staining using a 10× objective.

Figure 6:
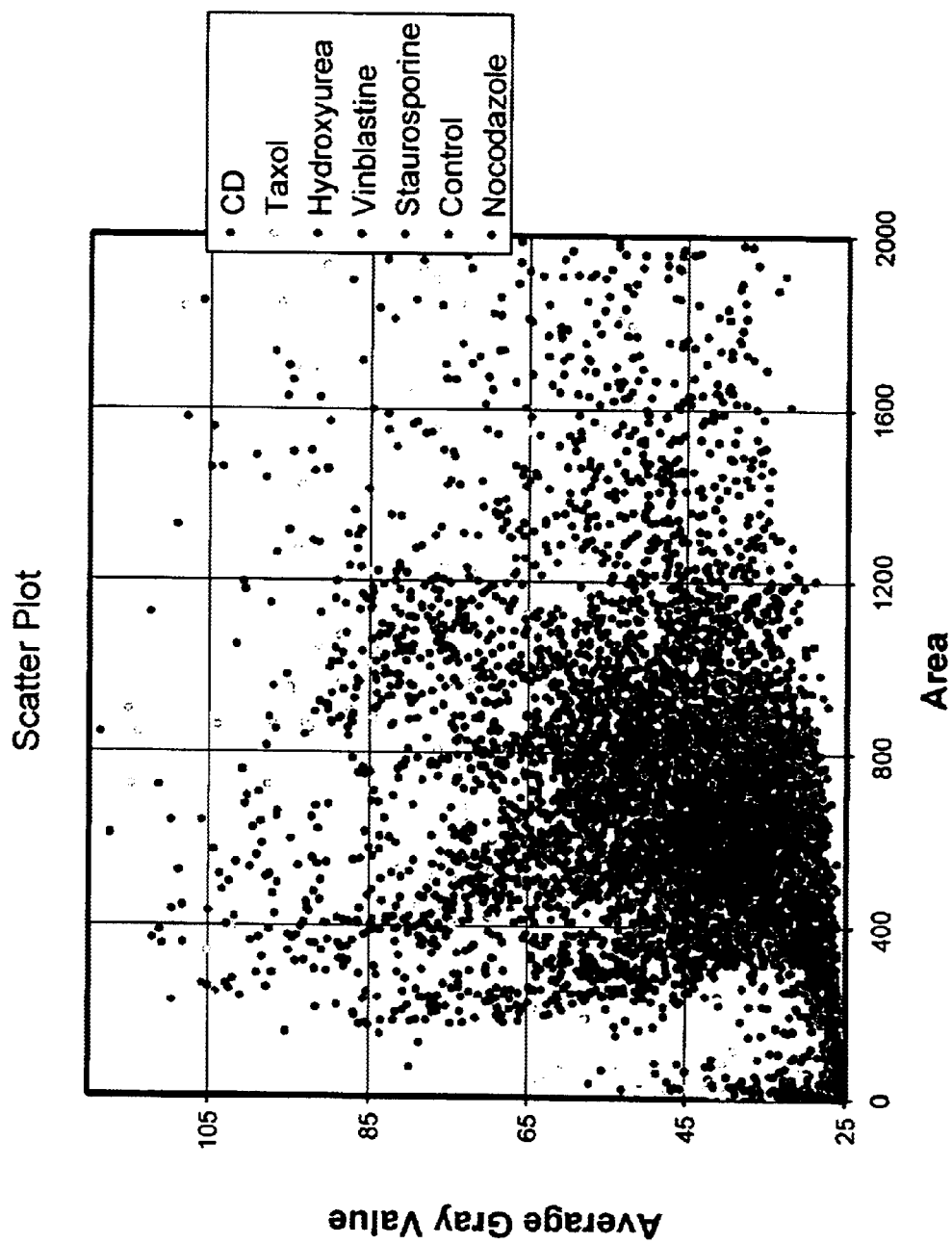
FIG. 6 illustrates a graph of quantified descriptors of effects of manipulations on cell cytoarchitecture in a particular experiment.

The results of this experiment were that the low magnification images taken of Hoechst were run through the automated image analysis method described in the first experiment. Plots of the average gray value and area were made of each compound. FIG. 6 shows the scatter plots of the compounds. The scatter plots of each compound are visually distinct. For example, cells treated with CD are smaller than control, and cells treated with Hydroxyurea are larger and brighter. Furthermore, the number of cells per well was very different (data not shown).

Based upon the results of this experiment, it can be concluded that these initial attempts at automatically identifying changes in cellular morphology demonstrate that the effects of different compounds can be distinguished. This method can also be used to count adherent cells.

The next steps that can be taken based upon the results of this experiment are to develop clustering algorithms that will assign statistically meaningful values to the representative two dimensional data shown in FIG. 5, and even more complicated clustering of all of the multidimensional data that can be extracted across one, and multiple markers.

In a fourth experiment was performed to obtain high magnification images of two markers in the presence of drugs. In this experiment, HeLa cells were treated with 80 generic compounds with known mechanism of action. The quantitative methods described in the first experiment were applied to the Hoechst images.

Approximately 5,000 HeLa cells per well were plated in a Costar black walled 96 well tissue culture treated plate and left to recover in the incubator for 24 hours. After this time, 10 ug/mL of each compound from the Killer Plate from Microsource Discovery Systems (Gaylordsville, Conn.) was added to different wells at a 1:100 addition in DMSO. The cells were incubated in the presence of drug for 24 more hours. After 24 hours, the cells were removed and fixed as in the first experiment. In addition to being labeled with Hoechst 33342 (against chromatin), cells were also labeled with 1 unit of rhodamine-conjugated phalloidin (against actin) for 30 minutes.

The 96 well plate was imaged twice. Once, 9 images per well were collected of the Hoechst staining using a 10× objective. After this, one image per well of both the phalloidin and Hoechst staining was collected using a 40× objective.

Figure 7:
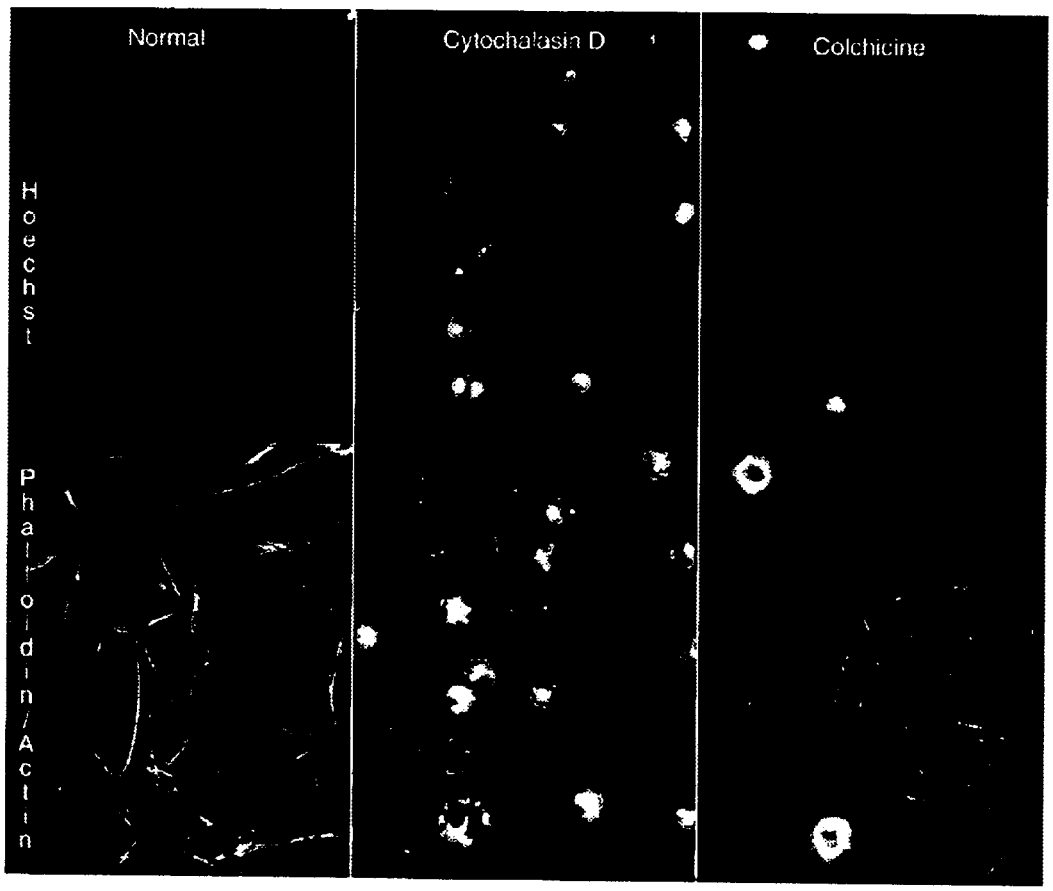
FIG. 7 illustrates effects of external agents on cell cytoarchitecture in a particular experiment.

The resulting high magnification images were analyzed qualitatively and distinct pattern differences were detected in both the Hoechst and phalloidin images. FIG. 7 shows three example images from the experiment. The top row is the Hoechst staining, and the bottom row is the phalloidin staining from the same well. The columns show the images from wells treated with just DMSO (control), cytochalasin D, and Colchicine. Notice that the morphology of each marker is different in the presence of each drug. Interestingly, there is an effect in the morphology of the chromatin in the Hoechst image of cytochalasin D, which effects the actin cytoskeleton (and thus there is an expected effect in the phalloidin image). Also, there is an effect on the actin cytoskeleton, compared to control, in the presence of colchicine that effects the microtubule network.

The low magnification images were analyzed as described in the first experiment, and different patterns were seen in both the average gray value vs. area plots, and in the number of cells per well (data not shown). Based upon the results of this experiment, it can be concluded that the fact that changes in patterns of a marker that is "down-stream" from the mechanism of action of a compound are detectable illustrates the efficacy of this approach.

The next step based upon the results of this experiment is to develop automated image analysis protocols for actin and other markers.

A fifth experiment was performed to test quadruple labeling of 9 different cell lines grown in normal conditions. In this experiment, NCI-H460, A549, MDA-MD-231, MCF-7, SK-OV-3, OVCAR-3, A498, U-2 OS, and HeLa cells were plated. Then, the cells were fixed and stained for DNA, tubulin, actin, and Golgi markers.

| Action | Active Ingredient/Notes | Buffer | Vol/well | Desired Time | Temp |
|---|---|---|---|---|---|
| Remove media | NOTE: gently by pipetttng, not aspiration | | | | |
| Fix | 4% Formaldehyde | PBS | 100 μl | 20 min | rt |
| Wash | | TBS | 100 μl | 5 min | rt |
| Wash | | TBS | 100 μl | 5 min | rt |
| Permeablize | 0.1% Triton X-100 | TBS | 100 μl | 10 min | rt |
| Permeablize | 0.1% Triton X-100 | TBS | 100 μl | 10 min | rt |
| Block | % BSA % Serum Filter sterilize before use | TBS w/ azide | 100 μl | 1 hr or o/n | rt or 4° C. |
| Primary Antibody | 1:1000 dilution of DM1α | TBS + 1% BSA + 0.1% TX-100 | 50 μ1 | 1 hr or o/n | rt or 4° C. |
| Wash | | TBS | 100 μl | 5 min | rt |
| Wash | | TBS | 100 μl | 5 min | rt |
| Wash | | TBS | 100 μl | 5 min | rt |
| Fluorescent Stain | FITC lens culinaris 1:500 Rhodamine-Phalloidin | TBS + 1% BSA + 0.1% TX-100 | 50 μl | 1 hr. | rt, dark |

-continued

| Action | Active Ingredient/Notes | Buffer | Vol/well | Desired Time | Temp |
|---|---|---|---|---|---|
| Wash | 1:500 CY5 goat anti-mouse 1:100 | PBS | 100 μl | 5 min | rt, dark |
| Hoechst | 1:1000 dilution of 5mg/ml | TBS | 100 μl | 15 min | rt, dark |
| Wash | | PBS | 100 μl | 5 min | rt, dark |
| Wash | | PBS | 100 μl | 5 min | rt, dark |
| Wash | | PBS | 100 μl | 5 min | rt, dark |
| Store | | PBS | 200 μl | 1 month | 4° C. |

Cells were plated out at different densities for 48 hours. Cells were fixed and labeled by the above method. Cells were imaged using an automated imaging macro that collected 9 images from each marker using a 10× objective. Higher magnification images were collected of a few cells for demonstration purposes.

In this experiment, each cell line demonstrated different morphological patterns as determined by phase. For example, A549 cells are much more compacted than OVCAR-3 cells as determined by phase contract imaging (data not shown). The different fluorescent markers showed even bigger differences between different cell lines.

Figure 8:
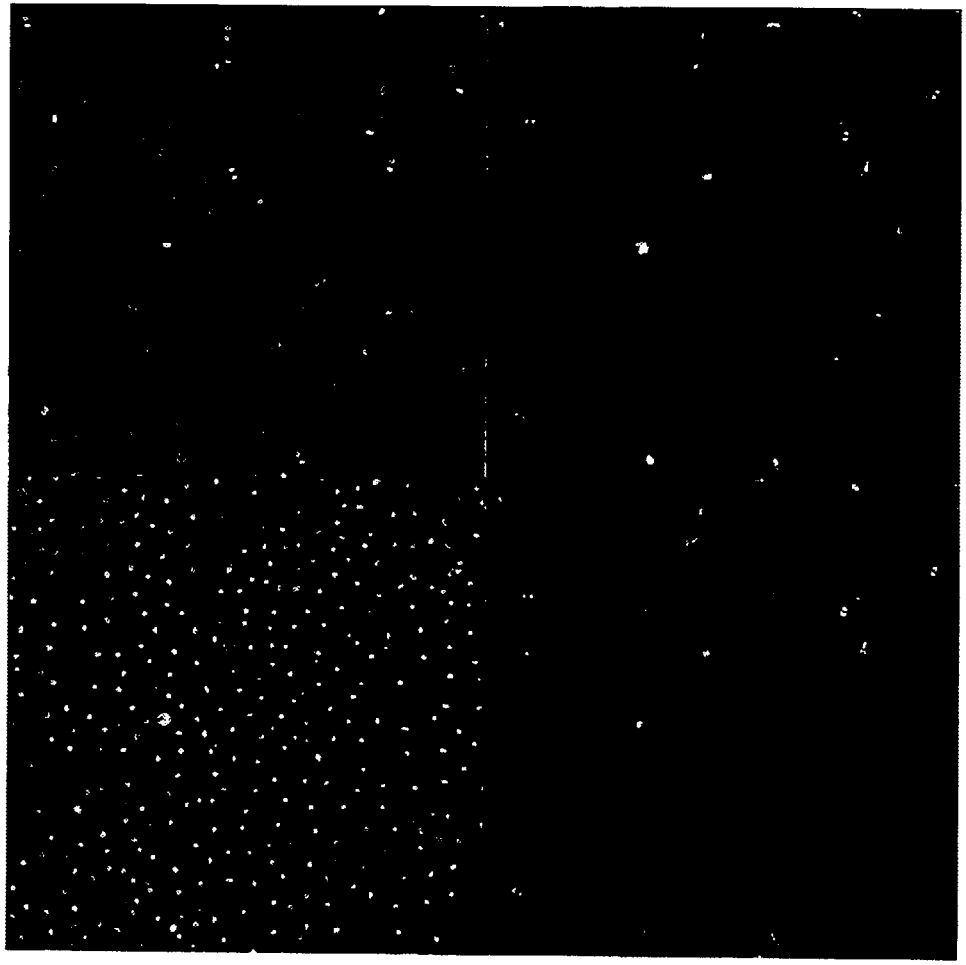
FIG. 8 illustrates 4 panels, one for each marker for a plurality of A549 cells in a particular experiment.
Figure 9:
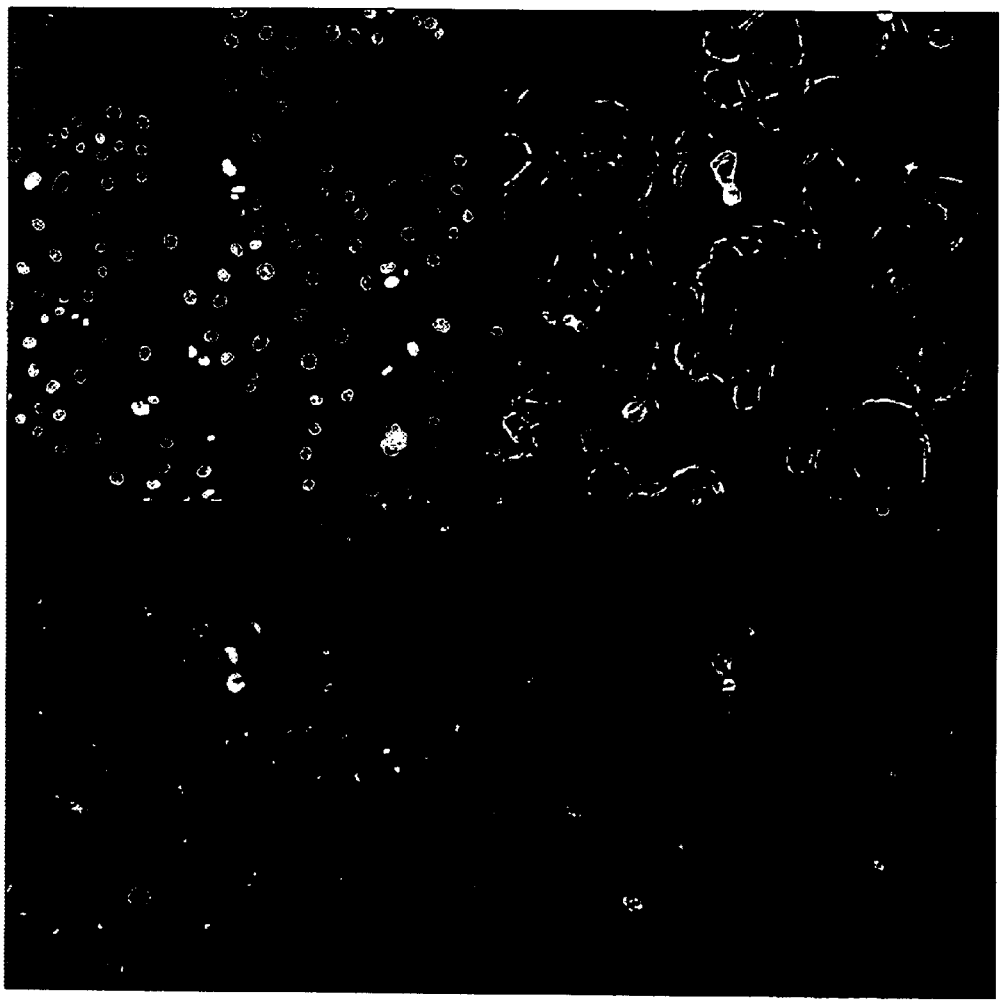
FIG. 9 illustrates 4 panels, one for each marker for a plurality of OVCAR-3 cells in a particular experiment.

FIGS. 8 and 9 show 4 panels of each marker for A549 (FIG. 8) and OVCAR-3 cells (FIG. 9). The markers are Hoechst (upper left), Phalloidin (upper right), Lens culinaris (lower left), and DM1 a antibody (lower right). The following table summarizes the qualitative differences between these images:

| Marker | A549 | OVCAR3 |
|---|---|---|
| Hoechst/DNA | small | large |
| Phalloidin/actin | fuzzy | crisp - many stress fibers |
| Lens culinaris/Golgi | compact | Disperse/punctate |
| DM1alpha/Tubulin | perinuclear | evenly distributed |

Figure 10:
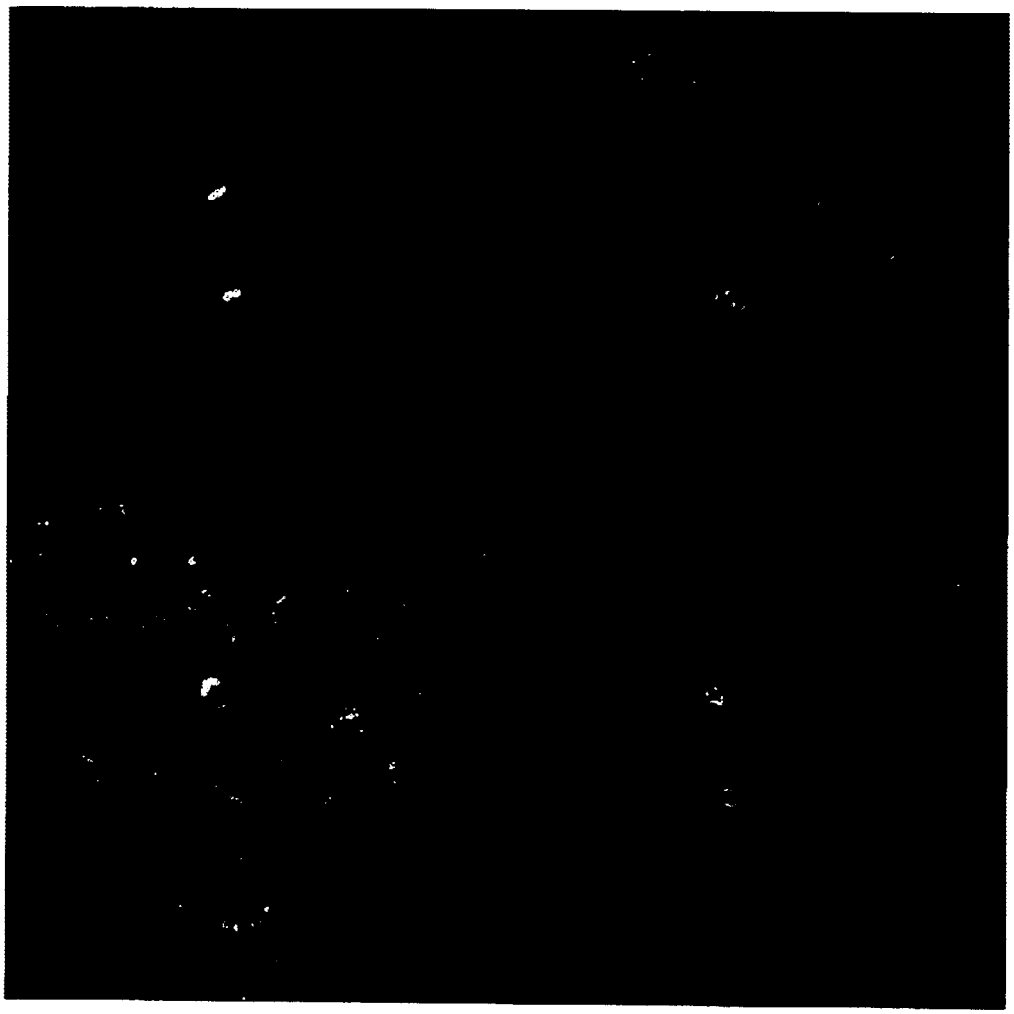
FIG. 10 illustrates 4 panels for each marker for a plurality of OVCAR-3 cells at 20× in a particular experiment.
Figure 11:
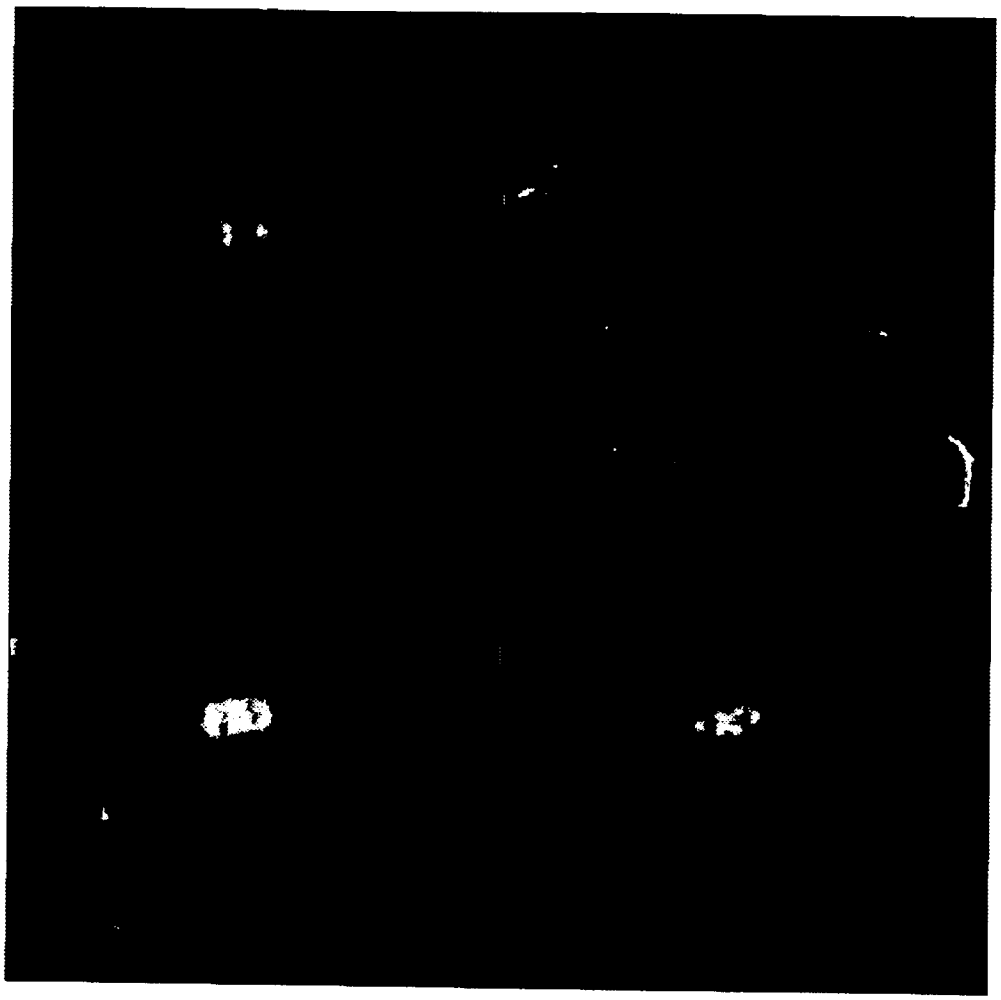
FIG. 11 illustrates 4 panels for each marker for a plurality of OVCAR-3 cells at 40× in a particular experiment.

Higher magnification images were taken of the OVCAR3 cells. FIG. 10 shows the same markers at 20×, and FIG. 11 shows the markers at 40×. While the highest magnification images show the most detail, these images illustrate that very little morphological information is lost in the 10× images.

These data exemplify the differences in morphology seen between different cell types. Thus the automated image analysis software will have to be customized for each marker in each cell type. Different drugs should effect these morphologies differentially.

The next steps based upon the results of this experiment are to customize and develop an automated quantification for each marker and cell line.

A sixth experiment was conducted with a more sophisticated software package and to develop more flexible image recognition algorithms. In this experiment, prototype image features extraction was performed using Matlab programming language with image toolbox and SDC morphology toolboxes. Algorithms are being developed that will automatically identify objects on images and to measure various morphological and intensity parameters of these objects. Since at present it is not known which of the measurements will be most useful for subsequent clustering, many different measurements for each of the cellular markers were acquired.

An example of a MatLab program called "AnalyseDNA" that takes as an input an unlimited number of images, identifies individual objects in these images based on either their intensities, or based on edge-detection algorithms, and extracts a number of morphological and intensity characteristics of these objects is provided in a particular embodiment according to the present invention. It will be understood that other programs could also be used in other embodiments without departing from the scope of the present invention. Thus, the copy of this program reproduced below is intended to be representative but not limiting:

Listing of the AnalyseDNA.m Program and of Some of the Supporting Subroutines

```
function files_analysed = AnalyseDNA(filermask, outpath, nx,
ny, filter_range, dext, modifier, sfname)
% AnalyseDNA performs measurements on files of DNA images
% V1. EV 2-11-99; 2-15-99; 2-16-99
%
% files_analysed = AnalyseDNA(filemask, outpath, nx, ny,
filter_range, dext, modifier, sfname)
%
% PARAMETERS:
%   ALL PARAMETERS ARE OPTIONAL
%
%   FILEMASK - mask for file names to be analyzed
INCLUDING PATH(for example c:\images\*.tif)
%   DEFAULT '.\*.tif' (all *.tif files in the current directory).
%
%   OUTPATH - path to a directory where all the output
files will be placed.
%   DEFAULT - output is saved in the same directory which
contains images
%
%   NX, NY - number of individual images in montage images
along X and Y axes (DEFAULT 1)
%
%   FILTER_RANGE - 3 col-wide array (or [ ]). Specifies how
data is filtered when summary is calculated
%   this parameter internally is passed to GetDNAData and
then to GetSummaryData - see these
%   functions for details. For example: [2 2 Inf; 6 100
8000] will case all raws of data for which
%       values in column 2 are less than 2 and all raws
where values in column 6 are less than 100 or
%       more than 8000 to be excluded from all
calculations of a summary.
%   DEFAULT - [ ] (means do not filter, summarize all data)
%
%   DEXT - string. Extension for data files being saved.
%   DEFAULT 'dat';
%
%   MODIFIER - this modifier is 'SUMMARY', summary file is created;
%   'SUMMARY ONLY' - only summary is generated, data
for individual files are not saved
%
%   sfname - string. File name of a summary file
%   DEFAULT 'summary[date].dat'
%
% OUTPUT:
%
%   AnalyseDNA works on image files or montages. For each
image file it creates a tab-delimits file of measured
%   parameters of all the objects in the montage with the
same base name as a montage file and extension specified
%   by dext parameter (or .dat by default) and file
'errors[date].err' - with the list of files that matched the
%   filemask but could not be processed.
%   If 'summary' or 'summary only' modifier is specified,
it also creates a single file 'summary[date].dat' (or
%   different extension, if specified by DEXT) which
```

-continued

```
contains summary information for all analyzed files.
%
%    ALL OUTPUT FILES are saved in a directory specified by
OUTPATH parameter
%
%    RETURNS *files_analysed* - number of files that have
been successfully processed.
%
%    Column designations in the output files are described
in GetDNAData
%
%    FILE NAME CONVENTIONS
%    AnalyseDNA attempts to identify a number for each file
to identify the file in summary output.
%    It does that by looking for the first space or
underscore, followed by a number and then takes
%    as many successive numbers as it can find. If it fails
to identify a number it assigns a
%    default which is -1
%
%
%    SEE ALSO GetDNAData, GetSummaryData
%
%    TO DO improve error handling in opening and writing
files (GLOBAL error_file ?)
%         include procedures for writing text headers into
the output files
if nargin > 8
   error ('Wrong number of input parameters');
end
if nargout >1
    error ('Wrong number of output parameters: only one
allowed');
end
% set defaults
need_summary = 0;
summary_only = 0;
use_default_outpath = 0;
datestring = datestr(floor(now));
it nargin == 7     % set default summary file name
    sfname = ['summary' deblank(datestring)]; % extension
will be appended later based on dext
        if deblank(upper(modifier)) == 'SUMMARY'
            need_summary = 1;
        elseif deblank(upper(modifier)) == 'SUMMARY ONLY'
            need_summary = 1;
            summary_only = 1;
        else
            error(['Wrong parameter: unknown modifier '
modifier]);
        end
end
if nargin == 5
    % default data tile extension
    set dext = 'dat';
end
it nargin == 4
    % default filter range
    filter_range = [ ];
end
if nargin == 3
    ny = 1; % default number to images in montage along Y
end
if nargin == 2
    nx = 1;
end
it nargin == 1
    use_default_outpath = 1;
end
if nargin == 0
    filemask = '*.tif'
end
% check parameters
if ( ~ischar(filemask) | ~ischar(dext) | ~ischar(sfname) )
        error('Wrong parameter type: filename, filepath,
dext and sfname should be strings');
end
if ( ( size(nx) ~= [1 1] ) | ( size(ny) ~= [1 1]) )
    error ('Wrong parameter type: nx and ny should be scalars
(1x1 arrays) ');
end
if (~isempty(filter_range) & size(filter_range, 2) ~= 3)
    error ('Wrong parameter type: filter range should be [ ]
or 3 - cols-wide array');
end
% end testing parameters
% Generate list of files to process
datapath = getpath(filemask);
if use_default_outpath == 1
    outpath = datapath;
end
if exist(outpath, 'dir') ~= 7
    error(['Path ' outpath, 'not found. Exiting..']);
elseif exist(datapath, 'dir') ~= 7
    error(['Path ' datapath, 'not found. Exiting..']);
end
sfname = makefullname(outpath, sfname, dext);
if need_summary == 1
    if exist(sfname, 'file')
        disp(['File ', sfname, 'already exists!']);
        input('Press ^C to abort, Enter to delete and
continue');
        delete(sfname);
    end
end
flist = FileList(getfname(filemask), datapath);
numfiles = size(flist, 1); % total number of files to
process
disp(['About to process ', num2str(numfiles), 'files']);
%DEBUG - commented out "input" to run from Wrod
input('Press ^C to abort, Enter to continue');
% main loop where the job gets done:
error_file = makefullname(outpath, ['error' datestring
'.err']);
num_processed = 0;
num_error = 0;
for i = 1:numfiles
    % first generate file name for a data output file
    current_fullname = flist(i, :); % full name with path and
extension
    current_datafile = makefullname(outpath,
makefname(getbasefname(current_fullname), dext) );
    %extract number from a filename
    fnumber = getfilenumber(current_fullname);
    % load an imagefile, record errors
    read_error = 0;
    try
        I = imread(current_fullname);
        %DEBUG
        disp (['Image file #', num2str(fnumber), 'loaded']);
    catch
        % record file-opening error in an error_file
        read_error = 1;
        num_error = num_error +1;
        msg = [current_fullname ': ' lasterr];
        add_error_msg(error_file, msg);
    end
    % extract and write data to a file in outpath
    if read_error ~= 1
        if (need_summary == 0)
            %DEBUG
            disp (['Starting analysis of file #',
num2str(fnumber), '.']);
            current_data = GetDNAData(I, nx, ny, fnumber);
            %DEBUG
            disp (['Finished analysis of file #',
num2str(fnumber), '.']);
            %load current_data.mat 'current_data';
            write_data(current_data, current_datafile);
        else %summary needed
            %DEBUG
            [current_data, current_summary] = GetDNAData(I, nx,
```

```
ny, fnumber, filter_range);
        %load current_data.mat 'current_data';
        %load current_summary.mat 'current_summary';
        write_summary(current_summary, sfname);
        if summary_only ~= 1
            write_data(current_data, current_datafile);
        end
    end
end
end % of the main for loop
num_processed = numfiles - num_error;
%=======================end function AnalyseDNA( )
%==========================================
%==========================
function result = add_error_msg(filename, msg)
% adds string MSG to an errorfile FILENAME
% returns 1 if success, 0 if failure
err_FID = fopen(filename, 'at');
if err_FID == -1
    warning(['Can not open error file ' filename]);
else
    fprintf(err_FID, '%s\n', msg);
    fclose(err_FID);
end
%=====================end function add_error_masg( )
%====================================
%====================================
function N = getfilenumber(fname)
% returns the first number extracted from a file name
(string) or -1 if fails to extract any number
numbers = NumbersFromString( getfname(fname) ); % vector of
all numbers encoded in the name
                % (but not in the path, even if present)
if isempty(numbers)
    N = (-1); % return -1 if no numbers found in the name
else
    N = numbers(1);
end
%=================== end function getfilenumber( )
%====================================
%====================================
function result = write_data(data_array, file_name)
% writes data in a data_array in a tab-delimited ascii file.
% result is 0 if success and -1 if failure
% if file_name exists, overwrites it
result = -1;
try
    fid = fopen(file_name, 'wt');
    if fid ~= -1
        for k = 1:size(data_array, 1)
            fprintf(fid, '%g\t', data_array(k, :) );
            fprintf(fid, '\n');
        end
        test = fclose(fid);
        result = -1;
catch
    result = -1;
end
%=================== end function write_data( )
%====================================
%====================================
function result = write_summary (s_vector, file_name)
% appends summary vector s_vector to a file_name (ASCII tab-
delimited file).
% if file_name does not exist, creates it.
% result is 0 if success and -1 if failure
%
result = -1;
try
    % debug
    fid = fopen(file_name, 'at');
    result = fprintf(fid, '%g\t', s_vector);
    result = fprintf(fid, '\n');
    result = fclose(fid);
    result = 0;
catch
    result = -1;
end
%=================== end function write_summary( )
%====================================
function Data = GetObjectsData(I, Ilabel)
% GetObjectsData returns array measurements of objects in
image "I" masked by "Ilabel"
% EV 2-3-99; 2-10-99
% OData = GetObjectsData(I, Ilabel) returns an array of
morphological and intensity measurements
% taken from a grayscale image "I". Objects are
identified on a mask image Ilabel, usually
%    created by bwlabel( )
% OUTPUT:
% Each row in the output array OData represents individual
object
% columns contain the following measurements:
%
%   1 - Index ("number" of an object);    8 - Solidity;
%   2 - X coordinate of the center of mass;  9 - Extent;
%   3 - Y coordinate of the center of mass;  10 - Total
Intensity;
%   4 - Total Area (in pixels);           11 - Avg.
Intensity;
%   5 - Ratio of MajorAxis/MinorAxis;     12 - Median
Intensity;
%   6 - Eccentricity;                     13 - Intensity of
20% bright pixel
%   7 - EquivDiameter;                    14 - Intensity of
80% bright pixel
%
% For details on morphological parameters see information on
MatLab imfeature( );
% Intensity parameters are either obvious or are documented
in comments in this file.
% Procedures in this file are documented in notebook file
"MATLAB Measuring Nuclei (1) 1-29-98.doc"
if (nargin ~= 2)
    error('function requires exactly 2 parameters');
end
if (nargout ~= 1)
    error ('function has 1 output argument (array X by 14)');
end
% finished checking arguments
% first collect morphological parameters in a structure
array:
ImStats = imfeature(Ilabel, 'Area', 'Centroid',
'MajorAxisLength', . . .
    'MinorAxisLength', 'Eccentricity', 'EquivDiameter', . . .
    'Solidity', 'Extent', 8 );
% now convert it into array (matrix) while collecting
intensity data for each object:
%preallocate output array:
numobjects = size(ImStats, 1);
OData = zeros(numobjects, 14);
%now convert ImStats into array and add intensity data to it
for k=1:numobjects
    OData(k, 1) = k;
    OData(k, 2) = ImStats(k).Centroid(1);
    OData(k, 3) = ImStats(k).Centroid(2);
    OData(k, 4) = ImStats(k).Area;
    OData(k, 5) = (ImStats(k).MajorAxisLength) /
(ImStats(k).MinorAxisLength);
    OData(k, 6) = ImStats(k).Eccentricity ;
    OData(k, 7) = ImStats(k).EquivDiameter;
    OData(k, 8) = ImStats(k).Solidity;
    OData(k, 9) = ImStats(k).Extent;
    % now collect and assign intensity parameters from
image I
    object_pixels = find( Ilabel == k);
    object_area = size(object_pixels, 1); %same as total
number of pixels in the object
    object_intensities = double(I(object_pixels)); % need
to convert to double to do math
    sorted_intensities = sort(object_intensities); % will
```

```
-continued need to get median, 20% and 80% pixels
      total_intensity = sum(object_intensities, 1);
      avg_intensity = total_intensity / object_area;
      median_intensity = sorted_intensities( floor(
object_area/2 ) + 1 );
      pix20 = sorted_intensities( floor(object_area*0.2)+1 )
; %brightest pixel among dimmest 20%
      pix80 = sorted_intensities( floor(object_area*0.8)+1 )
;
      OData(k, 10) = total_intensity;
      OData(k, 11) = avg_intensity;
      OData(k, 12) = median_intensity;
      OData(k, 13) = pix20; %brightest pixel among dimmest
20%
      OData(k, 14) = pix80; %dimmest pixel among brightest
20%
end %for
%=================== end function
GetObjectsData( ) ==============================
function Imask = MaskDNA1 (I);
% MaskDNA1 - generates binary mask for cell nuclei through
edge detection
% EV 1-22-99; 2-6-99; 2-10-99
% Imask = MaskDNA1 (I)
% PARAMETERS
%    I - intensity image (grayscale)
% OUTPUT
%    Imask - BW image with objects from I
%
% For more details see Notebook Matlab_DNA_masking1_1-22-
99.doc
% Uses SDC Morphology Toolbox V0.7
if (nargin ~= 1)
    error('Wrong number of input parameters');
end
if (nargout ~= 1)
    error('Wrong number of output parameters: one output
argument should be provided');
end
Imask = edge(I, 'canny');
Imask = mmdil(Imask, mmsecross(1));
Imask = mmero ( mmclohole(Imask,mmsecross(1)));
Imask = mmedgeoff(Imask, mmsecross(1));
% note that mmedgeoff this command removed FILLED OBJECTS
but not touching OUTLINES.
% these outlines can be removed by filtering:
Imask = medfilt2(Imask, [5 5]);
%=========end MaskDNA1=====================
```

Given the list of image files or montages of images as an input, this program creates an individual file for each image that contains the following quantitative measurements for all objects identified in the image:
1—Index ("number" of an object);
2—X coordinate of the center of mass;
3—Y coordinate -"-;
4—Total Area (in pixels);
5—Ratio of MajorAxis/MinorAxis;
6—Eccentricity;
7—EquivDiameter;
8—Solidity;
9—Extent;
10—Total Intensity;
11—Avg. Intensity;
12—Median Intensity;
13—Intensity of 20% bright pixel
14—Intensity of 80% bright pixel A fragment of an output for a single file, containing 9 images of cells stained for DNA and acquired with a 10× lens, is provided in a particular embodiment according to the present invention. It will be understood that other results could also be obtained in other embodiments without departing from the scope of the present invention. Thus, the copy of this example output file reproduced in Appendix A is intended to be representative but not limiting.

Figure 12:
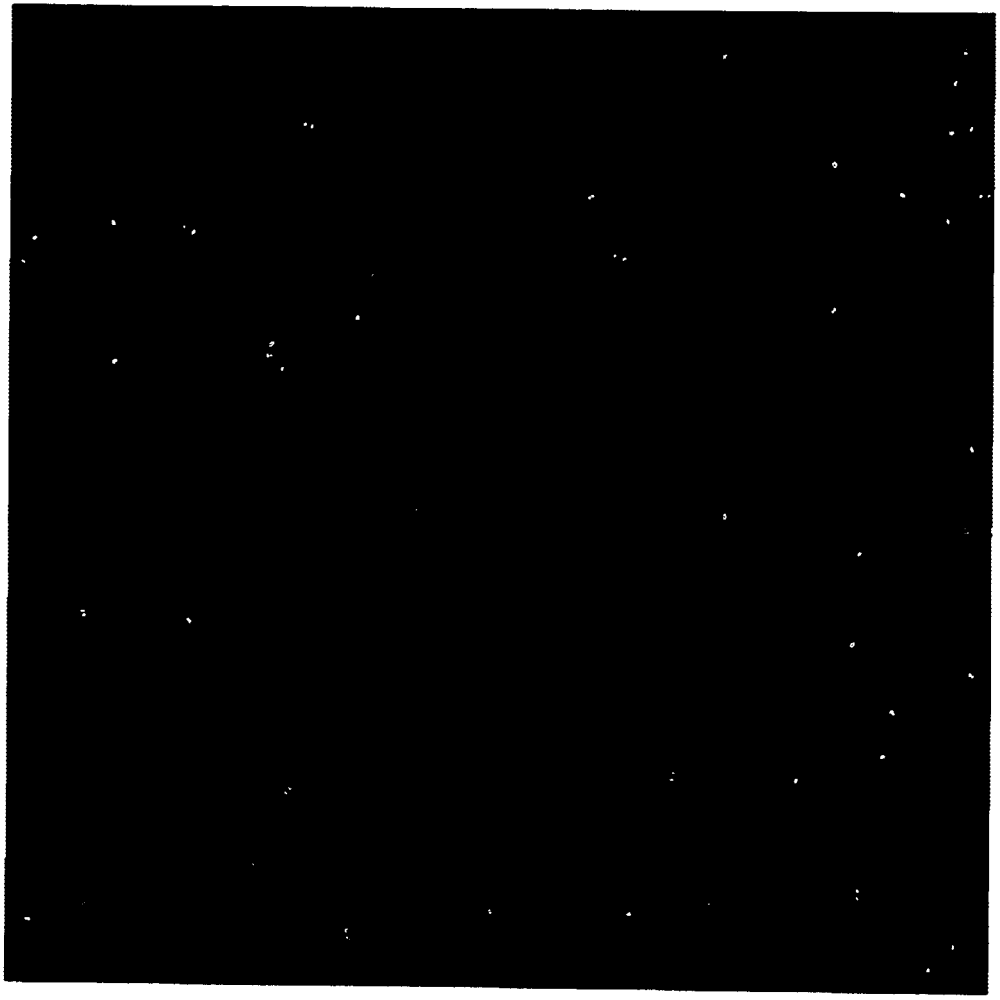
FIG. 12 illustrates a representative input for a morphometric analysis program in a particular embodiment according to the present invention.

A montage image that was used as a source to generate data in Appendix A is presented in FIG. 12. The same program also summarizes measurements across many files and performs statistical analysis of the summary data. It creates a summary file with the following data:
1—Image file number;
2—Average object Area (in pixels);
3—STD (standard deviation) of 2;
4—Avg. of Ratio of MajorAxis/MinorAxis;
5—STD of 4;
6—Avg. Eccentricity;
7—STD of 6;
8—Avg. EquivDiameter;
9—STD of 8;
10—Avg. of Solidity;
11—STD of 10;
12—Avg. of Extent;
13—STD of 11
14—Avg. of objects Total Intensity;
15—STD of 14
16—Avg. of objects Avg Intensity;
16—STD of 15
18—Avg. of objects Median intensity;
19—STD of 18
20—Avg. of objects intensity of 20% bright pixel;
21—STD of 19
22—Avg. of objects intensity of 80% bright pixel;
23—STD of 21

An example of summary output obtained by running AnalyseDNA against 10 montage files is provided in a particular embodiment according to the present invention. It will be understood that other results could also be obtained in other embodiments without departing from the scope of the present invention. Thus, the copy of this example output file reproduced in Appendix B is intended to be representative but not limiting.

A seventh experiment was conducted in order to use sequence analysis algorithms to analyze features of cell images. In this experiment, HeLa cells were treated for 24 hour with several different compounds, fixed, and stained with a fluorescent DNA dye. One image of these cells was acquired for each of the treatments and following morphometric parameters were measured:

Resulting measurements were arranged into a string of numbers and reduced to a pseudo-nucleic acid sequence using following rules: At any given position in the sequence a number was substituted by "t" (a code for thymidine) if its value is among highest 25% of the values at the corresponding position in the data set, "g" if it is between 50% and 25%, "c" if it is between 75% and 50%, and "a" if it belongs to lowest 25% of values. Thus one sequence was generated per treatment as illustrated in FIG. 13.

Resulting sequences were clustered using an AlignX module commercial software package Vector NTI which uses a Neighbor Joining algorithm for sequence clustering.

Resulting dendrogram is presented in FIG. 13. On the dendrogram the closest "leafs" correspond to the closest pseudo-sequences. Interestingly, compounds with similar mechanisms of action cluster together on the dendrogram. Another example of the generation of pseudo-sequences and clustering is shown in FIG. 14.

CONCLUSION

Although the above has generally described the present invention according to specific computer based software and systems, the present invention has a much broader range of applicability. In particular, the present invention is not limited to a particular kind of data about a cell, but can be applied to virtually any cellular data where an understanding about the workings of the cell is desired. Thus, in some embodiments, the techniques of the present invention could provide information about many different types of cells, substances, and genetic processes of all kinds. Of course, one of ordinary skill in the art would recognize other variations, modifications, and alternatives.

What is claimed is:

1. A computer program product for populating a database with information related to an effect of a manipulation on a plurality of cells from a plurality of different cell lines, wherein said cells are from a plurality of sites in a spatial orientation, each of the sites being capable of holding a plurality of cells to be imaged, said computer program product comprising:

code for receiving, from said plurality of sites, a site at a time, one or more images of a plurality of components from a plurality of cells from a plurality of different cell lines. wherein said plurality of cells are in a plurality of stages of the cell cycle, said stages of the cell cycle including at least one selected from interphase, G0 phase, G1 phase, S phase, G2 phase, M phase, prophase, prometaphase, metaphase, anaphase, and telophase and wherein said plurality of cells have been exposed to said manipulation;

code for determining from said images of said manipulated cells a plurality of features of said plurality of components from said plurality of cells for each of said plurality of different cell lines code for determining a plurality of descriptors for each of said plurality of different cell lines by combining said plurality of features for each of said plurality of different cell lines;

code for statistically analyzing said plurality of descriptors to determine the effect of said manipulation on said plurality of cells of said plurality of different cell lines;

code for populating a database with said descriptors and said statistical analysis; and a computer readable storage medium for holding the codes.

2. The computer program product of claim 1 wherein said plurality of components are selected from the group consisting of a protein, a protein modification, a nucleic acid, a lipid, a carbohydrate, a sub-cellular structure, and an organelle.

3. The computer program product of claim 1 wherein said images are each a digitized representation of said plurality of manipulated cells.

4. The computer program product of claim 3 wherein said digitized representation provides a density value of said plurality of manipulated cells.

5. The computer program product of claim 1 wherein said descriptors comprise numeric or logical values.

* * * * *